(12) United States Patent
Bagger et al.

(10) Patent No.: US 9,132,147 B2
(45) Date of Patent: Sep. 15, 2015

(54) USE OF LNA APOB ANTISENSE OLIGOMERS FOR THE TREATMENT OF ACUTE CORONARY SYNDROMES

(75) Inventors: Yu Bagger, Birkerod (DK); Ellen Marie Straarup, Birkerod (DK)

(73) Assignee: Roche Innovation Center Copenhagen

( * ) Notice: Subject to any disclaimer, the term of this patent is extended or adjusted under 35 U.S.C. 154(b) by 0 days.

(21) Appl. No.: 13/142,929

(22) PCT Filed: Dec. 18, 2009

(86) PCT No.: PCT/EP2009/067561
§ 371 (c)(1),
(2), (4) Date: Sep. 26, 2011

(87) PCT Pub. No.: WO2010/076248
PCT Pub. Date: Jul. 8, 2010

(65) Prior Publication Data
US 2012/0122955 A1    May 17, 2012

Related U.S. Application Data

(60) Provisional application No. 61/141,848, filed on Dec. 31, 2008.

(51) Int. Cl.
| | | |
|---|---|---|
| A61K 48/00 | (2006.01) | |
| C07H 21/02 | (2006.01) | |
| C07H 21/04 | (2006.01) | |
| A61K 31/712 | (2006.01) | |
| A61K 31/713 | (2006.01) | |
| C12N 15/113 | (2010.01) | |

(52) U.S. Cl.
CPC ............ *A61K 31/712* (2013.01); *A61K 31/713* (2013.01); *C12N 15/113* (2013.01); *C12N 2310/11* (2013.01); *C12N 2310/322* (2013.01)

(58) Field of Classification Search
CPC .............................. C12N 15/113; A61K 48/00
See application file for complete search history.

(56) References Cited

U.S. PATENT DOCUMENTS

| | | | |
|---|---|---|---|
| 2008/0242629 A1 | 10/2008 | Crooke et al. | |
| 2010/0280099 A1* | 11/2010 | Elmen | 514/44 A |
| 2012/0183581 A1* | 7/2012 | Yaworski et al. | 424/400 |

FOREIGN PATENT DOCUMENTS

| | | | |
|---|---|---|---|
| WO | WO2006/036916 | 4/2006 | |
| WO | WO2007/031081 | 3/2007 | |
| WO | WO2007/107162 | 9/2007 | |
| WO | WO2008/113830 | 9/2008 | |
| WO | WO 2009/114475 A2 * | 9/2009 | 514/44 |
| WO | WO2010/076248 | 7/2010 | |

OTHER PUBLICATIONS

Gregory G. Schwartz et al., "Effects of atorvastatin on early recurrent ischemic events in acute coronary syndromes: The MIRACL study: A randomized controlled trial," Journal of the American Medical Association 285:1711-1718 (2001).

International Search Report and Written Opinion for corresponding PCT Application No. PCT/EP2009/067561, dated Mar. 23, 2010, pp. 1-15.

Cannon C.P. et al., "Intensive Versus Moderate Lipid Lowering with Statins after Acute Coronary Syndromes," New England Journal of Medicine, 350(15):1495-1504 (2004).

Kastelein John J.P. et al., "Potent reduction of apolipoprotein B and low-density lipoprotein cholesterol by short-term administration of an antisense inhibitor of apolipoprotein B," Circulation, 114(16):1729-1735 (2006).

Crooke Rosanne M. et al., "An apolipoprotein B antisense oligonucleotide lowers LDL cholesterol in hyperlipidemic mice without causing hepatic steatosis," Journal of Lipid Research, 46(5):872-884 (2005).

Soutschek J. et al., "Therapeutic silencing of an endogenous gene by systemic administration of modified siRNAs," Nature, 432(7014):173-178 (2004).

Rosengren et al., "Serum cholesterol and long-term prognosis in middle-aged men with myocardial infarction and angina pectoris: A 16-year follow-up of the Primary Prevention Study in Goteborg, Sweden," European Heart Journal, 18(5):754-761 (1997).

* cited by examiner

*Primary Examiner* — Amy Bowman

(74) *Attorney, Agent, or Firm* — Fish & Richardson P.C.

(57) ABSTRACT

The present invention relates to the use of LNA antisense apoB oligonucleotides for the treatment of acute coronary syndrome.

11 Claims, 2 Drawing Sheets

Figure 1:
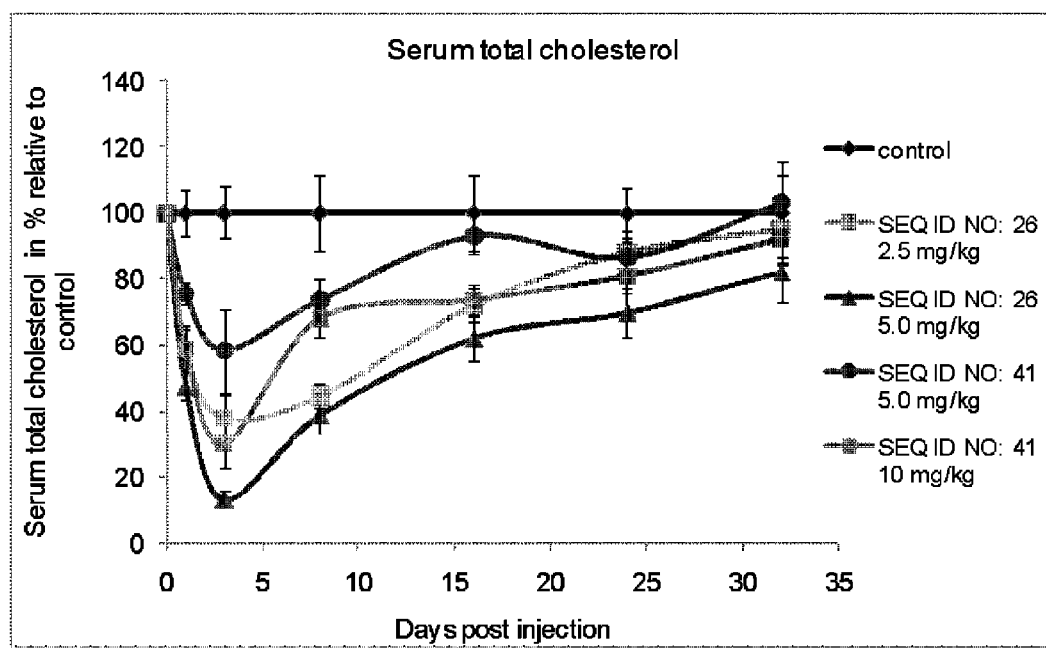

SEQUENCE LISTING

<160> NUMBER OF SEQ ID NOS: 137

<210> SEQ ID NO 1
<211> LENGTH: 14
<212> TYPE: DNA
<213> ORGANISM: Artificial
<220> FEATURE:
<223> OTHER INFORMATION: Oligomer sequence

<400> SEQUENCE: 1
tctgaagtcc atga                                                        14

<210> SEQ ID NO 2
<211> LENGTH: 14
<212> TYPE: DNA
<213> ORGANISM: Artificial
<220> FEATURE:
<223> OTHER INFORMATION: Oligomer sequence

<400> SEQUENCE: 2
ggatcaaata taag                                                        14

<210> SEQ ID NO 3
<211> LENGTH: 14
<212> TYPE: DNA
<213> ORGANISM: Artificial
<220> FEATURE:
<223> OTHER INFORMATION: Oligomer sequence

<400> SEQUENCE: 3
gttgacactg tctg                                                        14

<210> SEQ ID NO 4
<211> LENGTH: 12
<212> TYPE: DNA
<213> ORGANISM: Artificial
<220> FEATURE:
<223> OTHER INFORMATION: Oligomer sequence

<400> SEQUENCE: 4
gttgacactg tc                                                          12

<210> SEQ ID NO 5
<211> LENGTH: 14
<212> TYPE: DNA
<213> ORGANISM: Artificial
<220> FEATURE:
<223> OTHER INFORMATION: Oligomer sequence

<400> SEQUENCE: 5
gactgcctgt tctc                                                        14

<210> SEQ ID NO 6
<211> LENGTH: 13
<212> TYPE: DNA
<213> ORGANISM: Artificial
<220> FEATURE:
<223> OTHER INFORMATION: Oligomer sequence

<400> SEQUENCE: 6
cgttggagta agc                                                         13

<210> SEQ ID NO 7
<211> LENGTH: 14
<212> TYPE: DNA
<213> ORGANISM: Artificial

```
<220> FEATURE:
<223> OTHER INFORMATION: Oligomer sequence

<400> SEQUENCE: 7
gcgttggagt aagc                                                        14

<210> SEQ ID NO 8
<211> LENGTH: 14
<212> TYPE: DNA
<213> ORGANISM: Artificial
<220> FEATURE:
<223> OTHER INFORMATION: Oligomer sequence

<400> SEQUENCE: 8
ctctgtgatc cagg                                                        14

<210> SEQ ID NO 9
<211> LENGTH: 14
<212> TYPE: DNA
<213> ORGANISM: Artificial
<220> FEATURE:
<223> OTHER INFORMATION: Oligomer sequence

<400> SEQUENCE: 9
ggactctgtg atcc                                                        14

<210> SEQ ID NO 10
<211> LENGTH: 14
<212> TYPE: DNA
<213> ORGANISM: Artificial
<220> FEATURE:
<223> OTHER INFORMATION: Oligomer sequence

<400> SEQUENCE: 10
ctgtttgagg gact                                                        14

<210> SEQ ID NO 11
<211> LENGTH: 14
<212> TYPE: DNA
<213> ORGANISM: Artificial
<220> FEATURE:
<223> OTHER INFORMATION: Oligomer sequence

<400> SEQUENCE: 11
gagatggcag atgg                                                        14

<210> SEQ ID NO 12
<211> LENGTH: 14
<212> TYPE: DNA
<213> ORGANISM: Artificial
<220> FEATURE:
<223> OTHER INFORMATION: Oligomer sequence

<400> SEQUENCE: 12
gctggtgttg ccac                                                        14

<210> SEQ ID NO 13
<211> LENGTH: 13
<212> TYPE: DNA
<213> ORGANISM: Artificial
<220> FEATURE:
<223> OTHER INFORMATION: Oligomer sequence

<400> SEQUENCE: 13
cagatccttg cac                                                         13
```

```
<210> SEQ ID NO 14
<211> LENGTH: 14
<212> TYPE: DNA
<213> ORGANISM: Artificial
<220> FEATURE:
<223> OTHER INFORMATION: Oligomer sequence

<400> SEQUENCE: 14
ccagatcctt gcac                                                         14

<210> SEQ ID NO 15
<211> LENGTH: 12
<212> TYPE: DNA
<213> ORGANISM: Artificial
<220> FEATURE:
<223> OTHER INFORMATION: Oligomer sequence

<400> SEQUENCE: 15
accttttgag ac                                                           12

<210> SEQ ID NO 16
<211> LENGTH: 14
<212> TYPE: DNA
<213> ORGANISM: Artificial
<220> FEATURE:
<223> OTHER INFORMATION: Oligomer sequence

<400> SEQUENCE: 16
caatgttcag actg                                                         14

<210> SEQ ID NO 17
<211> LENGTH: 14
<212> TYPE: DNA
<213> ORGANISM: Artificial
<220> FEATURE:
<223> OTHER INFORMATION: Oligomer sequence

<400> SEQUENCE: 17
cctgcaatgt tcag                                                         14

<210> SEQ ID NO 18
<211> LENGTH: 14
<212> TYPE: DNA
<213> ORGANISM: Artificial
<220> FEATURE:
<223> OTHER INFORMATION: Oligomer sequence

<400> SEQUENCE: 18
tagggctgta gctg                                                         14

<210> SEQ ID NO 19
<211> LENGTH: 14
<212> TYPE: DNA
<213> ORGANISM: Artificial
<220> FEATURE:
<223> OTHER INFORMATION: Oligomer sequence

<400> SEQUENCE: 19
gttggtctac ttca                                                         14

<210> SEQ ID NO 20
<211> LENGTH: 14
<212> TYPE: DNA
<213> ORGANISM: Artificial
<220> FEATURE:
<223> OTHER INFORMATION: Oligomer sequence
```

```
<400> SEQUENCE: 20
ccaaccaatt tctc                                                          14

<210> SEQ ID NO 21
<211> LENGTH: 14
<212> TYPE: DNA
<213> ORGANISM: Artificial
<220> FEATURE:
<223> OTHER INFORMATION: Oligomer sequence

<400> SEQUENCE: 21
gtcaattgta aagg                                                          14

<210> SEQ ID NO 22
<211> LENGTH: 14
<212> TYPE: DNA
<213> ORGANISM: Artificial
<220> FEATURE:
<223> OTHER INFORMATION: Oligomer sequence

<400> SEQUENCE: 22
gtttaagaaa tcca                                                          14

<210> SEQ ID NO 23
<211> LENGTH: 12
<212> TYPE: DNA
<213> ORGANISM: Artificial
<220> FEATURE:
<223> OTHER INFORMATION: Oligomer sequence

<400> SEQUENCE: 23
cttagtgtta gc                                                            12

<210> SEQ ID NO 24
<211> LENGTH: 12
<212> TYPE: DNA
<213> ORGANISM: Artificial
<220> FEATURE:
<223> OTHER INFORMATION: Oligomer sequence

<400> SEQUENCE: 24
ggttcttagt gt                                                            12

<210> SEQ ID NO 25
<211> LENGTH: 14
<212> TYPE: DNA
<213> ORGANISM: Artificial
<220> FEATURE:
<223> OTHER INFORMATION: Oligomer sequence

<400> SEQUENCE: 25
ctggttctta gtgt                                                          14

<210> SEQ ID NO 26
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
```

<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 26
gcattggtat tca                                                        13

<210> SEQ ID NO 27
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 27
tctgaagtcc atga                                                       14

<210> SEQ ID NO 28
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 28
ggatcaaata taag                                                       14

<210> SEQ ID NO 29
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature

```
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 29
gttgacactg tctg                                                         14

<210> SEQ ID NO 30
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 30
caatgcctgt tctc                                                         14

<210> SEQ ID NO 31
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA
<220> FEATURE:
<221> NAME/KEY: misc_feature
<222> LOCATION: (14)..(14)
<223> OTHER INFORMATION: 5-methyl cytosine LNA
```

```
<400> SEQUENCE: 31
gactgcctgt tctc                                                          14

<210> SEQ ID NO 32
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (12)..(13)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA

<400> SEQUENCE: 32
cgttggagta agc                                                           13

<210> SEQ ID NO 33
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (14)..(14)
<223> OTHER INFORMATION: 5-methyl cytosine LNA

<400> SEQUENCE: 33
gcgttggagt aagc                                                          14

<210> SEQ ID NO 34
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
```

```
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA

<400> SEQUENCE: 34
ctctgtgatc cagg                                                  14

<210> SEQ ID NO 35
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (13)..(14)
<223> OTHER INFORMATION: 5-methyl cytosine LNA

<400> SEQUENCE: 35
ggactctgtg atcc                                                  14

<210> SEQ ID NO 36
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA

<400> SEQUENCE: 36
```

-continued

```
ctgtttgagg gact                                                           14

<210> SEQ ID NO 37
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 37
gagatggcag atgg                                                           14

<210> SEQ ID NO 38
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA
<220> FEATURE:
<221> NAME/KEY: misc_feature
<222> LOCATION: (14)..(14)
<223> OTHER INFORMATION: 5-methyl cytosine LNA

<400> SEQUENCE: 38
gctggtgttg ccac                                                           14

<210> SEQ ID NO 39
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
```

```
<222> LOCATION: (1)..(1)
<223> OTHER INFORMATION: 5-methyl cytosine LNA
<220> FEATURE:
<221> NAME/KEY: misc_feature
<222> LOCATION: (12)..(13)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA

<400> SEQUENCE: 39
cagatccttg cac                                                         13

<210> SEQ ID NO 40
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA
<220> FEATURE:
<221> NAME/KEY: misc_feature
<222> LOCATION: (14)..(14)
<223> OTHER INFORMATION: 5-methyl cytosine LNA

<400> SEQUENCE: 40
ccagatcctt gcac                                                        14

<210> SEQ ID NO 41
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 41
gttgacactg tc                                                          12
```

```
<210> SEQ ID NO 42
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 42
accttttgag ac                                                         12

<210> SEQ ID NO 43
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 43
cctgcaatgt tcag                                                       14

<210> SEQ ID NO 44
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
```

-continued

```
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA

<400> SEQUENCE: 44
tagggctgta gctg                                                      14

<210> SEQ ID NO 45
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA

<400> SEQUENCE: 45
gttggtctac ttca                                                      14

<210> SEQ ID NO 46
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(2)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(12)
<223> OTHER INFORMATION: 5-methyl cytosine LNA
<220> FEATURE:
<221> NAME/KEY: misc_feature
<222> LOCATION: (14)..(14)
<223> OTHER INFORMATION: 5-methyl cytosine LNA

<400> SEQUENCE: 46
ccaaccaatt tctc                                                      14

<210> SEQ ID NO 47
```

```
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 47
gtcaattgta aagg                                                        14

<210> SEQ ID NO 48
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (12)..(13)
<223> OTHER INFORMATION: 5-methyl cytosine LNA

<400> SEQUENCE: 48
gtttaagaaa tcca                                                        14

<210> SEQ ID NO 49
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
```

```
<222> LOCATION: (12)..(12)
<223> OTHER INFORMATION: 5-methyl cytosine LNA

<400> SEQUENCE: 49
cttagtgtta gc                                                          12

<210> SEQ ID NO 50
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units

<400> SEQUENCE: 50
ggttcttagt gt                                                          12

<210> SEQ ID NO 51
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA
<220> FEATURE:
<221> NAME/KEY: misc_feature
<222> LOCATION: (12)..(14)
<223> OTHER INFORMATION: LNA units, such as beta-D-oxy LNA units

<400> SEQUENCE: 51
ctggttctta gtgt                                                        14

<210> SEQ ID NO 52
<211> LENGTH: 16
<212> TYPE: DNA
<213> ORGANISM: Artificial
<220> FEATURE:
<223> OTHER INFORMATION: Oligomer sequence

<400> SEQUENCE: 52
ggtattcagt gtgatg                                                      16

<210> SEQ ID NO 53
<211> LENGTH: 16
<212> TYPE: DNA
<213> ORGANISM: Artificial
<220> FEATURE:
<223> OTHER INFORMATION: Oligomer sequence
```

```
<400> SEQUENCE: 53
attggtattc agtgtg                                                    16

<210> SEQ ID NO 54
<211> LENGTH: 16
<212> TYPE: DNA
<213> ORGANISM: Artificial
<220> FEATURE:
<223> OTHER INFORMATION: Oligomer sequence

<400> SEQUENCE: 54
ttgttctgaa tgtcca                                                    16

<210> SEQ ID NO 55
<211> LENGTH: 16
<212> TYPE: DNA
<213> ORGANISM: Artificial
<220> FEATURE:
<223> OTHER INFORMATION: Oligomer sequence

<400> SEQUENCE: 55
tcttgttctg aatgtc                                                    16

<210> SEQ ID NO 56
<211> LENGTH: 16
<212> TYPE: DNA
<213> ORGANISM: Artificial
<220> FEATURE:
<223> OTHER INFORMATION: Oligomer sequence

<400> SEQUENCE: 56
tggtattcag tgtgat                                                    16

<210> SEQ ID NO 57
<211> LENGTH: 16
<212> TYPE: DNA
<213> ORGANISM: Artificial
<220> FEATURE:
<223> OTHER INFORMATION: Oligomer sequence

<400> SEQUENCE: 57
ttggtattca gtgtga                                                    16

<210> SEQ ID NO 58
<211> LENGTH: 16
<212> TYPE: DNA
<213> ORGANISM: Artificial
<220> FEATURE:
<223> OTHER INFORMATION: Oligomer sequence

<400> SEQUENCE: 58
cattggtatt cagtgt                                                    16

<210> SEQ ID NO 59
<211> LENGTH: 16
<212> TYPE: DNA
<213> ORGANISM: Artificial
<220> FEATURE:
<223> OTHER INFORMATION: Oligomer sequence

<400> SEQUENCE: 59
gcattggtat tcagtg                                                    16

<210> SEQ ID NO 60
<211> LENGTH: 16
```

```
<212> TYPE: DNA
<213> ORGANISM: Artificial
<220> FEATURE:
<223> OTHER INFORMATION: Oligomer sequence

<400> SEQUENCE: 60
agcattggta ttcagt                                                      16

<210> SEQ ID NO 61
<211> LENGTH: 16
<212> TYPE: DNA
<213> ORGANISM: Artificial
<220> FEATURE:
<223> OTHER INFORMATION: Oligomer sequence

<400> SEQUENCE: 61
cagcattggt attcag                                                      16

<210> SEQ ID NO 62
<211> LENGTH: 16
<212> TYPE: DNA
<213> ORGANISM: Artificial
<220> FEATURE:
<223> OTHER INFORMATION: Oligomer sequence

<400> SEQUENCE: 62
tcagcattgg tattca                                                      16

<210> SEQ ID NO 63
<211> LENGTH: 16
<212> TYPE: DNA
<213> ORGANISM: Artificial
<220> FEATURE:
<223> OTHER INFORMATION: Oligomer sequence

<400> SEQUENCE: 63
ttcagcattg gtattc                                                      16

<210> SEQ ID NO 64
<211> LENGTH: 16
<212> TYPE: DNA
<213> ORGANISM: Artificial
<220> FEATURE:
<223> OTHER INFORMATION: Oligomer sequence

<400> SEQUENCE: 64
gttcagcatt ggtatt                                                      16

<210> SEQ ID NO 65
<211> LENGTH: 16
<212> TYPE: DNA
<213> ORGANISM: Artificial
<220> FEATURE:
<223> OTHER INFORMATION: Oligomer sequence

<400> SEQUENCE: 65
agttcagcat tggtat                                                      16

<210> SEQ ID NO 66
<211> LENGTH: 16
<212> TYPE: DNA
<213> ORGANISM: Artificial
<220> FEATURE:
<223> OTHER INFORMATION: Oligomer sequence

<400> SEQUENCE: 66
```
aagttcagca ttggta                                                          16

<210> SEQ ID NO 67
<211> LENGTH: 16
<212> TYPE: DNA
<213> ORGANISM: Artificial
<220> FEATURE:
<223> OTHER INFORMATION: Oligomer sequence

<400> SEQUENCE: 67
aaagttcagc attggt                                                          16

<210> SEQ ID NO 68
<211> LENGTH: 16
<212> TYPE: DNA
<213> ORGANISM: Artificial
<220> FEATURE:
<223> OTHER INFORMATION: Oligomer sequence

<400> SEQUENCE: 68
atttccatta agttct                                                          16

<210> SEQ ID NO 69
<211> LENGTH: 16
<212> TYPE: DNA
<213> ORGANISM: Artificial
<220> FEATURE:
<223> OTHER INFORMATION: Oligomer sequence

<400> SEQUENCE: 69
ggtatttcca ttaagt                                                          16

<210> SEQ ID NO 70
<211> LENGTH: 16
<212> TYPE: DNA
<213> ORGANISM: Artificial
<220> FEATURE:
<223> OTHER INFORMATION: Oligomer sequence

<400> SEQUENCE: 70
gactcaatgg aaaagt                                                          16

<210> SEQ ID NO 71
<211> LENGTH: 16
<212> TYPE: DNA
<213> ORGANISM: Artificial
<220> FEATURE:
<223> OTHER INFORMATION: Oligomer sequence

<400> SEQUENCE: 71
atgactcaat ggaaaa                                                          16

<210> SEQ ID NO 72
<211> LENGTH: 16
<212> TYPE: DNA
<213> ORGANISM: Artificial
<220> FEATURE:
<223> OTHER INFORMATION: Oligomer sequence

<400> SEQUENCE: 72
gctaacacta agaacc                                                          16

<210> SEQ ID NO 73
<211> LENGTH: 16
<212> TYPE: DNA
<213> ORGANISM: Artificial

```
<220> FEATURE:
<223> OTHER INFORMATION: Oligomer sequence

<400> SEQUENCE: 73
cactaagaac cagaag                                                       16

<210> SEQ ID NO 74
<211> LENGTH: 16
<212> TYPE: DNA
<213> ORGANISM: Artificial
<220> FEATURE:
<223> OTHER INFORMATION: Oligomer sequence

<400> SEQUENCE: 74
ctaagaacca gaagat                                                       16

<210> SEQ ID NO 75
<211> LENGTH: 16
<212> TYPE: DNA
<213> ORGANISM: Artificial
<220> FEATURE:
<223> OTHER INFORMATION: Oligomer sequence

<400> SEQUENCE: 75
tgaatcgggt cgcatc                                                       16

<210> SEQ ID NO 76
<211> LENGTH: 16
<212> TYPE: DNA
<213> ORGANISM: Artificial
<220> FEATURE:
<223> OTHER INFORMATION: Oligomer sequence

<400> SEQUENCE: 76
tgaatcgggt cgcatt                                                       16

<210> SEQ ID NO 77
<211> LENGTH: 21
<212> TYPE: RNA
<213> ORGANISM: Artificial
<220> FEATURE:
<223> OTHER INFORMATION: Oligomer sequence

<400> SEQUENCE: 77
gucaucacac ugaauaccaa u                                                 21

<210> SEQ ID NO 78
<211> LENGTH: 23
<212> TYPE: RNA
<213> ORGANISM: Artificial
<220> FEATURE:
<223> OTHER INFORMATION: Oligomer sequence

<400> SEQUENCE: 78
auugguauuc aguggauga cac                                                23

<210> SEQ ID NO 79
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
```

```
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units

<400> SEQUENCE: 79
ggtattcagt gtgatg                                            16

<210> SEQ ID NO 80
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units

<400> SEQUENCE: 80
attggtattc agtgtg                                            16

<210> SEQ ID NO 81
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units

<400> SEQUENCE: 81
attggtattc agtgtg                                            16

<210> SEQ ID NO 82
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
```

```
<223> OTHER INFORMATION: LNA units, such as beta-D-oxy LNA units
<220> FEATURE:
<221> NAME/KEY: misc_feature
<222> LOCATION: (14)..(15)
<223> OTHER INFORMATION: 5-methyl cytosine LNA units

<400> SEQUENCE: 82
ttgttctgaa tgtcca                                                          16

<210> SEQ ID NO 83
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units

<400> SEQUENCE: 83
tcttgttctg aatgtc                                                          16

<210> SEQ ID NO 84
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA units

<400> SEQUENCE: 84
cattggtatt cagtgt                                                          16

<210> SEQ ID NO 85
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
```

```
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units

<400> SEQUENCE: 85
gcattggtat tcagtg                                                  16

<210> SEQ ID NO 86
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 86
agcattggta ttcagt                                                  16

<210> SEQ ID NO 87
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA units
<220> FEATURE:
<221> NAME/KEY: misc_feature
<222> LOCATION: (14)..(14)
<223> OTHER INFORMATION: 5-methyl cytosine LNA units

<400> SEQUENCE: 87
cagcattggt attcag                                                  16
```

```
<210> SEQ ID NO 88
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA units
<220> FEATURE:
<221> NAME/KEY: misc_feature
<222> LOCATION: (4)..(4)
<223> OTHER INFORMATION: 5-methyl cytosine LNA units
<220> FEATURE:
<221> NAME/KEY: misc_feature
<222> LOCATION: (14)..(14)
<223> OTHER INFORMATION: 5-methyl cytosine LNA units

<400> SEQUENCE: 88
cagcattggt attcag                                                  16

<210> SEQ ID NO 89
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (15)..(15)
<223> OTHER INFORMATION: 5-methyl cytosine LNA units

<400> SEQUENCE: 89
atttccatta agttct                                                  16

<210> SEQ ID NO 90
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
```

```
<220> FEATURE:
<221> NAME/KEY: misc_feature
<222> LOCATION: (13)..(15)
<223> OTHER INFORMATION: LNA units, such as beta-D-oxy LNA units

<400> SEQUENCE: 90
ggtatttcca ttaagt                                                    16

<210> SEQ ID NO 91
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units

<400> SEQUENCE: 91
gactcaatgg aaaagt                                                    16

<210> SEQ ID NO 92
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units

<400> SEQUENCE: 92
atgactcaat ggaaaa                                                    16

<210> SEQ ID NO 93
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
```

```
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (15)..(15)
<223> OTHER INFORMATION: 5-methyl cytosine LNA units

<400> SEQUENCE: 93
gctaacacta agaacc                                                       16

<210> SEQ ID NO 94
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA units
<220> FEATURE:
<221> NAME/KEY: misc_feature
<222> LOCATION: (3)..(3)
<223> OTHER INFORMATION: 5-methyl cytosine LNA units

<400> SEQUENCE: 94
cactaagaac cagaag                                                       16

<210> SEQ ID NO 95
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (1)..(1)
<223> OTHER INFORMATION: 5-methyl cytosine LNA units

<400> SEQUENCE: 95
ctaagaacca gaagat                                                       16

<210> SEQ ID NO 96
<211> LENGTH: 16
<212> TYPE: DNA
<213> ORGANISM: Artificial
```

```
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 96
tgaatcgggt cgcatc                                                     16

<210> SEQ ID NO 97
<211> LENGTH: 16
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(16)
<223> OTHER INFORMATION: Phosphorothioate linkages
<220> FEATURE:
<221> NAME/KEY: misc_feature
<222> LOCATION: (1)..(4)
<223> OTHER INFORMATION: LNA units, such as beta-D-oxy LNA units
<220> FEATURE:
<221> NAME/KEY: misc_feature
<222> LOCATION: (13)..(15)
<223> OTHER INFORMATION: LNA units, such as beta-D-oxy LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 97
tgaatcgggt cgcatt                                                     16

<210> SEQ ID NO 98
<211> LENGTH: 16
<212> TYPE: DNA
<213> ORGANISM: Artificial
<220> FEATURE:
<223> OTHER INFORMATION: Oligomer sequence

<400> SEQUENCE: 98
cagcattggt attcag                                                     16

<210> SEQ ID NO 99
<211> LENGTH: 15
<212> TYPE: DNA
<213> ORGANISM: Artificial
<220> FEATURE:
<223> OTHER INFORMATION: Oligomer sequence

<400> SEQUENCE: 99
cagcattggt attca                                                      15

<210> SEQ ID NO 100
<211> LENGTH: 15
<212> TYPE: DNA
```

```
<213> ORGANISM: Artificial
<220> FEATURE:
<223> OTHER INFORMATION: Oligomer sequence

<400> SEQUENCE: 100
agcattggta ttcag                                                15

<210> SEQ ID NO 101
<211> LENGTH: 14
<212> TYPE: DNA
<213> ORGANISM: Artificial
<220> FEATURE:
<223> OTHER INFORMATION: Oligomer sequence

<400> SEQUENCE: 101
cagcattggt attc                                                 14

<210> SEQ ID NO 102
<211> LENGTH: 14
<212> TYPE: DNA
<213> ORGANISM: Artificial
<220> FEATURE:
<223> OTHER INFORMATION: Oligomer sequence

<400> SEQUENCE: 102
agcattggta ttca                                                 14

<210> SEQ ID NO 103
<211> LENGTH: 14
<212> TYPE: DNA
<213> ORGANISM: Artificial
<220> FEATURE:
<223> OTHER INFORMATION: Oligomer sequence

<400> SEQUENCE: 103
gcattggtat tcag                                                 14

<210> SEQ ID NO 104
<211> LENGTH: 13
<212> TYPE: DNA
<213> ORGANISM: Artificial
<220> FEATURE:
<223> OTHER INFORMATION: Oligomer sequence

<400> SEQUENCE: 104
cagcattggt att                                                  13

<210> SEQ ID NO 105
<211> LENGTH: 13
<212> TYPE: DNA
<213> ORGANISM: Artificial
<220> FEATURE:
<223> OTHER INFORMATION: Oligomer sequence

<400> SEQUENCE: 105
agcattggta ttc                                                  13

<210> SEQ ID NO 106
<211> LENGTH: 13
<212> TYPE: DNA
<213> ORGANISM: Artificial
<220> FEATURE:
<223> OTHER INFORMATION: Oligomer sequence

<400> SEQUENCE: 106
gcattggtat tca                                                  13
```

```
<210> SEQ ID NO 107
<211> LENGTH: 13
<212> TYPE: DNA
<213> ORGANISM: Artificial
<220> FEATURE:
<223> OTHER INFORMATION: Oligomer sequence

<400> SEQUENCE: 107
cattggtatt cag                                                        13

<210> SEQ ID NO 108
<211> LENGTH: 12
<212> TYPE: DNA
<213> ORGANISM: Artificial
<220> FEATURE:
<223> OTHER INFORMATION: Oligomer sequence

<400> SEQUENCE: 108
cagcattggt at                                                         12

<210> SEQ ID NO 109
<211> LENGTH: 12
<212> TYPE: DNA
<213> ORGANISM: Artificial
<220> FEATURE:
<223> OTHER INFORMATION: Oligomer sequence

<400> SEQUENCE: 109
agcattggta tt                                                         12

<210> SEQ ID NO 110
<211> LENGTH: 12
<212> TYPE: DNA
<213> ORGANISM: Artificial
<220> FEATURE:
<223> OTHER INFORMATION: Oligomer sequence

<400> SEQUENCE: 110
gcattggtat tc                                                         12

<210> SEQ ID NO 111
<211> LENGTH: 12
<212> TYPE: DNA
<213> ORGANISM: Artificial
<220> FEATURE:
<223> OTHER INFORMATION: Oligomer sequence

<400> SEQUENCE: 111
cattggtatt ca                                                         12

<210> SEQ ID NO 112
<211> LENGTH: 12
<212> TYPE: DNA
<213> ORGANISM: Artificial
<220> FEATURE:
<223> OTHER INFORMATION: Oligomer sequence

<400> SEQUENCE: 112
attggtattc ag                                                         12

<210> SEQ ID NO 113
<211> LENGTH: 15
<212> TYPE: DNA
<213> ORGANISM: Artificial
<220> FEATURE:
```

```
<223> OTHER INFORMATION: Oligomer sequence or LNA Oligomer
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 113
agcattggta ttcag                                                    15

<210> SEQ ID NO 114
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 114
agcattggta ttca                                                     14

<210> SEQ ID NO 115
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
```

```
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 115
agcattggta ttca                                                            14

<210> SEQ ID NO 116
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(2)
<223> OTHER INFORMATION: Phosphorothioate linkages
<220> FEATURE:
<221> NAME/KEY: misc_feature
<222> LOCATION: (3)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 116
agcattggta ttca                                                            14

<210> SEQ ID NO 117
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (4)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units
```

```
<400> SEQUENCE: 117
agcattggta ttca                                                        14

<210> SEQ ID NO 118
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 118
agcattggta ttca                                                        14

<210> SEQ ID NO 119
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 119
agcattggta ttca                                                        14

<210> SEQ ID NO 120
<211> LENGTH: 14
```

```
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 120
agcattggta ttca                                                   14

<210> SEQ ID NO 121
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(13)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 121
agcattggta ttca                                                   14

<210> SEQ ID NO 122
<211> LENGTH: 14
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units, such as beta-D-oxy LNA units
<220> FEATURE:
<221> NAME/KEY: misc_feature
<222> LOCATION: (12)..(14)
```

```
<223> OTHER INFORMATION: LNA units, such as beta-D-oxy LNA units
<220> FEATURE:
<221> NAME/KEY: misc_feature
<222> LOCATION: (3)..(3)
<223> OTHER INFORMATION: 5-methyl cytosine LNA units
<220> FEATURE:
<221> NAME/KEY: misc_feature
<222> LOCATION: (13)..(13)
<223> OTHER INFORMATION: 5-methyl cytosine LNA units

<400> SEQUENCE: 122
agcattggta ttca                                                           14

<210> SEQ ID NO 123
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 123
gcattggtat tca                                                            13

<210> SEQ ID NO 124
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 124
gcattggtat tca                                                            13
```

```
<210> SEQ ID NO 125
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(2)
<223> OTHER INFORMATION: Phosphorothioate linkages
<220> FEATURE:
<221> NAME/KEY: misc_feature
<222> LOCATION: (3)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 125
gcattggtat tca                                                        13

<210> SEQ ID NO 126
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(10)
<223> OTHER INFORMATION: Phosphorothioate linkages
<220> FEATURE:
<221> NAME/KEY: misc_feature
<222> LOCATION: (11)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 126
gcattggtat tca                                                        13

<210> SEQ ID NO 127
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
```

```
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (12)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 127
gcattggtat tca                                                          13

<210> SEQ ID NO 128
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 128
gcattggtat tca                                                          13

<210> SEQ ID NO 129
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
```

```
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 129
gcattggtat tca                                                           13

<210> SEQ ID NO 130
<211> LENGTH: 13
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(13)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 130
gcattggtat tca                                                           13

<210> SEQ ID NO 131
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 131
gcattggtat tc                                                            12

<210> SEQ ID NO 132
```

```
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 132
gcattggtat tc                                                         12

<210> SEQ ID NO 133
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(2)
<223> OTHER INFORMATION: Phosphorothioate linkages
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 133
gcattggtat tc                                                         12

<210> SEQ ID NO 134
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(10)
<223> OTHER INFORMATION: Phosphorothioate linkages
<220> FEATURE:
<221> NAME/KEY: misc_feature
```

```
<222> LOCATION: (11)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 134
gcattggtat tc                                                             12

<210> SEQ ID NO 135
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 135
gcattggtat tc                                                             12

<210> SEQ ID NO 136
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
```

-continued

```
<221> NAME/KEY: misc_feature
<222> LOCATION: (12)..(12)
<223> OTHER INFORMATION: 5-methyl cytosine LNA units

<400> SEQUENCE: 136
gcattggtat tc                                                    12

<210> SEQ ID NO 137
<211> LENGTH: 12
<212> TYPE: DNA
<213> ORGANISM: Artificial
<220> FEATURE:
<223> OTHER INFORMATION: Oligomer sequence or LNA Oligomer
<220> FEATURE:
<221> NAME/KEY: misc_feature
<222> LOCATION: (3)..(10)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units, such as beta-D-oxy LNA units
<220> FEATURE:
<221> NAME/KEY: misc_feature
<222> LOCATION: (11)..(12)
<223> OTHER INFORMATION: LNA units, such as beta-D-oxy LNA units
<220> FEATURE:
<221> NAME/KEY: misc_feature
<222> LOCATION: (2)..(2)
<223> OTHER INFORMATION: 5-methyl cytosine LNA units
<220> FEATURE:
<221> NAME/KEY: misc_feature
<222> LOCATION: (12)..(12)
<223> OTHER INFORMATION: 5-methyl cytosine LNA units

<400> SEQUENCE: 137
gcattggtat tc                                                    12
```

USE OF LNA APOB ANTISENSE OLIGOMERS FOR THE TREATMENT OF ACUTE CORONARY SYNDROMES

This application is the U.S. national stage under 35 USC §371 of International Application Number PCT/EP2009/067561, filed on 8 Dec. 2009, which claims priority to U. S. Application No. 61/141,848, filed on 31 Dec. 2008, the entire contents of which is hereby incorporated by reference.

TECHNICAL FIELD

The invention provides novel formulations and methods to treat or prevent acute coronary syndromes. The formulations and methods employ an antisense ApolipoproteinB compound comprising LNA residues.

BACKGROUND OF THE INVENTION

The management and treatment of myocardial infarction has changed dramatically since the first half of the 20$^{th}$ century, progressing from an era of bed rest and observation, to an emphasis on technology, including hemodynamic monitoring and balloon catheters, to an increased focus on thrombolytic therapy. (Antman and Braunwald, "Acute Myocardial Infarction" in Heart Disease, A Textbook of Cardiovascular Medicine, 61 edition, vol. 2, Braunwald et al., eds, 2001, W.B. Saunders Company, Philadelphia). Therapeutic approaches to treating cardiovascular diseases have evolved tremendously in the last 100 years accompanied by greater understanding of the underlying pathology.

Almost all myocardial infarctions result from coronary atherosclerosis, generally with superimposed coronary thrombosis. Slowly accumulating plaques can be asymptomatic due to the development of collateral vessels. However, atherosclerotic plaques, especially those rich in lipids, are prone to abrupt plaque rupture. Plaque rupture and associated endothelial injury cause the release of mediators such as thromboxane $A_2$, serotonin, adenosine diphosphate, thrombin, platelet activating factor, tissue factor and oxygen-derived free radicals. These mediators promote platelet aggregation and mechanical obstruction often leading to thrombus formation which interferes with blood flow and oxygen supply. Persistent and severe interferences with myocardial oxygen supply can lead to acute myocardial infarction. (See, Rioufol et al., 2002, Circulation 106:804, Timmis, 2003, Heart 89:1268-72).

The mainstay of atherosclerotic pharmacotherapy has been chronic therapy to prevent or slow the development of atherosclerotic plaques primarily by focusing on lowering LDL or "bad cholesterol" as a therapeutic endpoint. Statin therapy, for example, has greatly contributed to improved cardiovascular health; however, adverse effects such as rhabdomyolysis, remain an impediment. Furthermore, statins do little in an acute situation, for example, to reduce vulnerable, unstable atherosclerotic plaque during an ischemic episode. Acute treatment has largely relied on thrombolytics (such as tPA) and surgical intervention such a percutaneous transluminal coronary angioplasty (PTCA) and coronary artery bypass graft (CABG). While thrombolytics provide relief by decreasing or eliminating an occluding thrombus, they do not alter the underlying pathology. Interventions such as PTCA carry their own risks and are often unsuitable for patients in acute conditions. Hence current pharmacologic therapies do little to help patients once unstable plaque presents as a risk. (See, Newton and Krause 2002, Atherosclerosis S3:31-38).

Yet, despite the improved understanding of the pathophysiology of myocardial infarction and developments in atherosclerotic pharmacotherapy, safe and effective treatment modalities which have a fast onset of action to allow for treatment in the acute phase, and which do not have serious side effects when used for long term treatment, are still desired.

SUMMARY OF THE INVENTION

The invention provides a new use of antisense oligonucleotides targeting apolipoprotein B. The inventors have found novel hitherto unobserved characteristics of anti apo B antisense oligonucleotides comprising LNA, which characteristics will allow for new uses of such anti apo B antisense oligonucleotides. The present invention is based on the discovery that such molecules are able to provide a fast onset of action, and to reach a steady state of effect within a short time after onset of treatment, thereby providing significant advantages over existing therapies for treatment of acute coronary syndromes.

The invention provides for an oligomeric compound (oligomer) consisting of a total of 10-16 nucleobases, wherein the nucleobase sequence of said compound is present in the human apolipoprotein B gene or gene transcript, wherein said compound comprises at least 2 or at least 3 nucleotide analogues, wherein the compound is for treatment of acute coronary syndrome.

The invention provides for an oligomeric compound consisting of a total of 10-15 nucleobases, wherein the nucleobase sequence of said compound corresponds to a contiguous sub-sequence present in the human apolipoprotein B gene or gene transcript, wherein said compound comprises at least 2 or at least 3 nucleotide analogues, wherein the compound is for treatment of acute coronary syndrome.

The invention provides for a conjugate comprising the compound according to the invention and at least one non-nucleotide or non-polynucleotide moiety covalently attached to said compound, wherein the conjugate is for treatment of acute coronary syndrome.

The invention provides for a pharmaceutical composition comprising a compound or a conjugate according to the invention, and a pharmaceutically acceptable diluent, carrier or adjuvant.

The invention provides for a compound or a conjugate as according to the invention for use as a medicament for treatment of acute coronary syndrome.

The invention provides for the use of a compound or a conjugate according to the invention for the manufacture of a medicament for the treatment of abnormal levels of Apo-B100 or a disease or condition correlated thereto, wherein the disease or condition is a condition related to acute coronary syndrome. The invention provides for a medicament comprising the compound according to the invention or the conjugate according to the invention, for the treatment of abnormal levels of Apo-B100 or a disease or condition correlated thereto, such as atherosclerosis, hypercholesterolemia or hyperlipidemia, wherein the condition is acute coronary syndrome.

The invention provides for a method of treating a subject suffering from a disease or condition selected from atherosclerosis, hypercholesterolemia and hyperlipidemia, the method comprising the step of administering a pharmaceutical composition or conjugate or medicament according to the invention to a subject suffering from an acute coronary syndrome.

The invention provides for a method for down-regulation of apolipoprotein B, the method comprising the step of administering a pharmaceutical composition or conjugate or medicament according to the invention to a subject, such as a subject suffering from a medical condition selected from the group consisting of: atherosclerosis, hypercholesterolemia or hyperlipidemia, wherein any one of these conditions has resulted in an acute coronary syndrome.

The invention provides for a method for down-regulation of apolipoprotein B (ApoB) mRNA in a cell which is expressing said ApoB mRNA, said method comprising the step of administering the compound of the invention to said cell so as to down-regulate said ApoB mRNA, wherein the purpose of downregulating ApoB mRNA is to treat an acute coronary syndrome.

The invention provides for a method for down-regulation of apolipoprotein B (ApoB) protein in a cell which is expressing said ApoB protein, said method comprising the step of administering the compound of the invention to said cell so as to down-regulate said ApoB protein, wherein the purpose of downregulating ApoB protein is to treat an acute coronary syndrome.

FIGURE LEGENDS

FIG. 1: Serum total cholesterol measured before dosing, days 1, 3, 5, 8, 16, 24 and 32 days after a single injection of SEQ ID NO: 26 at 2.5 or 5 mg/kg or SEQ ID NO: 41 at 5 and 10 mg/kg FIG. 2: Serum total cholesterol and HDL cholesterol presented in % relative to control. SEQ ID NO 26 was injected once in a dosages of 1, 2.5 and 5 mg/kg, and SEQ ID NO: 41 was injected once in dosages of 1, 2.5, 5 and 10 mg/kg at day 0, Serum total cholesterol and HDL cholesterol was measured at one day after injection. TC=total cholesterol, HDL=High Density Lipoprotein

DETAILED DESCRIPTION OF THE INVENTION

1. Terms

U.S. provisional applications U.S. 61/186,388 and U.S.61/253,090, and 60/896,419 and 60/977,409, and PCT applications WO2007/031081 and WO2008113830, are hereby incorporated by reference in their entireties.

Oligomeric Compounds

The present invention employs oligomeric compounds, particularly antisense oligonucleotides, for use in inhibition of the function of nucleic acid molecules encoding apolipoprotein B (such as Apo-B100 and/or ApoB-48) which leads to a decrease in the number of functional proteins produced. The present invention is based on the observation by the inventors, that such molecules are able to provide a fast onset of action, and reach a steady state of effect on total cholesterol (steady state is in the context of the present invention defined as the time when a maximum effect on total cholesterol is reached by use of a particular chosen dosing regimen, after reaching the maximum effect, a continued stable effect may be obtained by continued administration dosages of the oligomer. Determination of the size of such maintenance dosages is routine work for the person skilled in the art.), within a short time after onset of treatment, thereby providing significant advantages over existing therapies for treatment of acute coronary disorders. The early onset of a steady state is as compared to existing treatment with compounds such as statins, and oligonucleotides not including LNA. Furthermore, the present invention provides methods and formulations adjusted to provide the fast onset of a steady state effect (within a week, such as within 1, 2, 3, 4, 5, 6 or 7 days after onset of treatment) without providing levels of compound that could provide toxicity in the liver or kidney.

ApoB100 inhibiting compounds that are useful in the present invention include but are not limited to compounds such as those disclosed in WO2007/031081 and WO2008/113830, which are incorporated by reference in their entireties. Especially preferred are the compounds disclosed in U.S. 60/896,419 and U.S. 60/977,409, attached hereto as Exhibits B and C, respectively, the entire specifications which are also incorporated by reference. However, the use of any LNA antisense apoB oligomeric compound would potentially be useful in the present invention. Further, in a particularly preferred embodiment, the motifs and compounds disclosed in U.S. 61/186,388 and U.S. 61/253,090, which are also incorporated herein by reference. Compounds of U.S. 61/186,388 and U.S. 61/253,090 are disclosed in Table 1 and Table 2 in the present application.

The term "LNA antisense" means that the oligomeric compound that it refers to comprises at least one LNA nucleotide analogue.

The present invention provides compositions and methods for modulating the expression of apolipoprotein B (ApoB100/Apo-B48). In particular, this invention relates to oligonucleotide compounds over specific motifs targeting apolipoprotein B. These motifs are SEQ ID NOS: 2-15, in particular SEQ ID NOS: 5, 9 and 13 of WO2007/031081. Specific designs of LNA containing oligonucleotide compounds are also disclosed. Specifically preferred compounds are SEQ ID NOS:17-40, and/or 41-49, in particular SEQ ID NOS: 16, 17, 26 and 34 of WO2007/031081. Motifs and compounds of WO2007/031081 are disclosed in Table 2 of the present application, and are all preferred. The compounds of the invention are potent inhibitors of apoliprotein mRNA and protein expression.

In one embodiment, the oligomer for use in the present invention comprise or consist of ISIS 301012 (5'GCCT-CAGTCTGCTTCGCACC-3' wherein the italicized bases are 2'-MOE modified ribonucleosides, and all cytokines are methylated at the C5 position.), although present data show that methods using this compound will not provide a steady state effect soon enough in order to be relevant for treatment of acute coronary syndrome (Yu et al. Circulation (2006); 114; 1729-1735).

In one embodiment, the oligomer for use in the present invention can comprise or consist of, or a sequence selected from the group consisting of SEQ ID NOS: 1-25 as listed in Table 1 below, wherein said oligomer (or contiguous nucleotide portion thereof) may optionally have one, two, or three mismatches against said selected sequence.

TABLE 1

| Test substance | Length | Target seq |
|---|---|---|
| SEQ ID NO: 1 | 14 | 5'-TCTGAAGTCCATGA-3' |
| SEQ ID NO: 2 | 14 | 5'-GGATCAAATATAAG-3' |
| SEQ ID NO: 3 | 14 | 5'-GTTGACACTGTCTG-3' |
| SEQ ID NO: 4 | 12 | 5'-GTTGACACTGTC-3' |
| SEQ ID NO: 5 | 14 | 5'-GACTGCCTGTTCTC-3' |
| SEQ ID NO: 6 | 13 | 5'-CGTTGGAGTAAGC-3' |
| SEQ ID NO: 7 | 14 | 5'-GCGTTGGAGTAAGC-3' |

TABLE 1-continued

| Test substance | Length | Target seq |
|---|---|---|
| SEQ ID NO: 8 | 14 | 5'-CTCTGTGATCCAGG-3' |
| SEQ ID NO: 9 | 14 | 5'-GGACTCTGTGATCC-3' |
| SEQ ID NO: 10 | 14 | 5'-CTGTTTGAGGGACT-3' |
| SEQ ID NO: 11 | 14 | 5'-GAGATGGCAGATGG-3' |
| SEQ ID NO: 12 | 14 | 5'-GCTGGTGTTGCCAC-3' |
| SEQ ID NO: 13 | 13 | 5'-CAGATCCTTGCAC-3' |
| SEQ ID NO: 14 | 14 | 5'-CCAGATCCTTGCAC-3' |
| SEQ ID NO: 15 | 12 | 5'-ACCTTTTGAGAC-3' |
| SEQ ID NO: 16 | 14 | 5'-CAATGTTCAGACTG-3' |
| SEQ ID NO: 17 | 14 | 5'-CCTGCAATGTTCAG-3' |
| SEQ ID NO: 18 | 14 | 5'-TAGGGCTGTAGCTG-3' |
| SEQ ID NO: 19 | 14 | 5'-GTTGGTCTACTTCA-3' |
| SEQ ID NO: 20 | 14 | 5'-CCAACCAATTTCTC-3' |
| SEQ ID NO: 21 | 14 | 5'-GTCAATTGTAAAGG-3' |
| SEQ ID NO: 22 | 14 | 5'-GTTTAAGAAATCCA-3' |
| SEQ ID NO: 23 | 12 | 5'-CTTAGTGTTAGC-3' |
| SEQ ID NO: 24 | 12 | 5'-GGTTCTTAGTGT-3' |
| SEQ ID NO: 25 | 14 | 5'-CTGGTTCTTAGTGT-3' |
| SEQ ID NO: 52 | | 5'-GGTATTCAGTGTGATG-3' |
| SEQ ID NO: 53 | | 5'-ATTGGTATTCAGTGTG-3' |
| SEQ ID NO: 54 | | 5'-TTGTTCTGAATGTCCA-3' |
| SEQ ID NO: 55 | | 5'-TCTTGTTCTGAATGTC-3' |
| SEQ ID NO: 56 | | 5'-TGGTATTCAGTGTGAT-3' |
| SEQ ID NO: 57 | | 5'-TTGGTATTCAGTGTGA-3' |
| SEQ ID NO: 58 | | 5'-CATTGGTATTCAGTGT-3' |
| SEQ ID NO: 59 | | 5'-GCATTGGTATTCAGTG-3' |
| SEQ ID NO: 60 | | 5'-AGCATTGGTATTCAGT-3' |
| SEQ ID NO: 61 | | 5'-CAGCATTGGTATTCAG-3' |
| SEQ ID NO: 62 | | 5'-TCAGCATTGGTATTCA-3' |
| SEQ ID NO: 63 | | 5'-TTCAGCATTGGTATTC-3' |
| SEQ ID NO: 64 | | 5'-GTTCAGCATTGGTATT-3' |
| SEQ ID NO: 65 | | 5'-AGTTCAGCATTGGTAT-3' |

As used herein, the term "target nucleic acid" encompasses DNA encoding the Apo-B100, RNA (including pre-mRNA and mRNA and mRNA edit) transcribed from such DNA, and also cDNA derived from such RNA.

The "target protein" is mammalian apolipoprotein B, preferably human apolipoprotein B. It will be recognised that as ApoB-100 and ApoB-48 both originate from the same genetic sequence, that the oligomeric compounds according to the invention may be used for down-regulation of either, or both forms of apolipoprotein B, and both ApoB-100 encoding mRNA, and the RNA edited form, which encodes Apo-B48.

As used herein, the term "gene" means the gene including exons, introns, non-coding 5" and 3" regions and regulatory elements and all currently known variants thereof and any further variants, which may be elucidated.

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

The terms "Oligomeric compound", which is interchangeable with the term "oligomer", "oligonucleotide", "oligo", and "oligonucleotide compound", refer, in the context of the present invention, to an oligomer, i.e. a nucleic acid polymer (e.g. ribonucleic acid (RNA) or deoxyribonucleic acid (DNA)) or nucleic acid analogue of those known in the art, preferably Locked Nucleic Acid (LNA), or a mixture thereof). This term includes oligonucleotides composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides, such as for instance, the ability to penetrate a cell membrane, good resistance to extra- and intracellular nucleases, high affinity and specificity for the nucleic acid target. The LNA analogue is particularly preferred, for example, regarding the above-mentioned properties. Therefore, in a highly preferable embodiment, the terms "oligomeric compound", "oligonucleotide", "oligo", "oligomer", and "oligonucleotide compound" according to the invention, are compounds which are built up of both nucleotide and nucleotide analogue units, such as LNA units to form a polymeric compound (oligomer) of between 10-15 (contiguous) nucleotides/nucleotide analogues.

The oligomeric compounds are preferably antisense oligomeric compounds, also referred to as 'antisense oligonucleotides' and 'antisense inhibitors'.

The antisense inhibitors are single stranded oligonucleotides. The single stranded oligonucleotides are preferably complementary to the corresponding region of the target nucleic acid.

Typically, single stranded 'antisense' oligonucleotides specifically interact with the mRNA of the target gene, causing either targeted degradation of the mRNA, for example via the RNaseH mechanism, or otherwise preventing translation.

By the term "unit" is understood a monomer.

The oligomeric compounds of the invention are capable of hybridizing either to the apolipoprotein B messenger RNA(s) and/or the sense or complementary mammalian apolipoprotein B (Apo-B) DNA strands. NCBI Accession No. NM_000384 provides an mRNA sequence for human apolipoprotein B. It is highly preferably that the oligomeric compound of the invention is capable of hybridising to the human apolipoprotein encoded by the nucleic acid disclosed in NCBI Accession No. NM_000384, or reverse complement thereof, including, in a preferred embodiment, mRNA nucleic acid targets derived from said human apolipoprotein.

The term "at least [an integer]" comprises the integers larger than or equal to said integer, such as 1, 2, 3, 4, 5, 6, 7, 8, 9, 10, 11, 12, 13, 14, 15, 16, 17, 18, 19, 20, 21 and so forth.

In an interesting embodiment, the 3' end of the compound of the invention comprises a nucleotide, rather than a nucleotide analogue.

In a preferred embodiment, the oligonucleotides are capable of hybridising against the target nucleic acid, such as an ApoB mRNA, to form a duplex with a $T_m$, of at least 30° C., such as at least 37° C., such as at least 40° C., at least 50° C., at least 55° C., at least 60° C., at least 65° C., at least 70° C., or at least 75° C. In one aspect, the $T_m$, is less than 85° C., such as less than 80° C., such as less than 75° C. or less than 70° C. In one aspect the $T_m$, is between 37° C. and 80° C., such as between 50 and 70° C. In one aspect the $T_m$ is between 30° C. and 40° C.

Measurement of $T_m$

A 3 μM solution of the compound in 10 mM sodium phosphate/100 mM NaCl/0.1 nM EDTA, pH 7.0 is mixed with its complement DNA or RNA oligonucleotide at 3 μM concentration in 10 mM sodium phosphate/100 mM NaCl/0.1 nM EDTA, pH 7.0 at 90° C. for a minute and allowed to cool down to room temperature. The melting curve of the duplex is then determined by measuring the absorbance at 260 nm with a heating rate of 1° C./min. in the range of 25 to 95° C. The $T_m$ is measured as the maximum of the first derivative of the melting curve.

In one embodiment the oligomeric compound according to the invention may target the DNA encoding mammalian ApoB.

The term "nucleobase" as used herein refers to both naturally occurring nucleotides, such as DNA and RNA nucleotides (units), and non-naturally occurring nucleotides, referred to as nucleotide analogue (units).

Length

The oligomers comprise or consist of a contiguous nucleotide sequence of a total of between 10, 11, 12, 13, 14, 15, 16, 17, 18, 19, 20, 21, 22, 23, 24, 25, 26, 27, 28, 29 or 30 contiguous nucleotides in length.

In some embodiments, the oligomers comprise or consist of a contiguous nucleotide sequence of a total of between 10-22, such as 12-18, such as 13-17 or 12-16, such as 13, 14, 15, 16 contiguous nucleotides in length.

In some embodiments, the oligomers comprise or consist of a contiguous nucleotide sequence of a total of 10, 11, 12, 13, or 14 contiguous nucleotides in length.

In some embodiments, the oligomer according to the invention consists of no more than 22 nucleotides, such as no more than 20 nucleotides, such as no more than 18 nucleotides, such as 15, 16 or 17 nucleotides. In some embodiments the oligomer of the invention comprises less than 20 nucleotides.

In a preferred embodiment, the oligomer is an LNA gapmer of 12, 13, 14, 15 or 16 contiguous nucleotides in length.

Gapmers

In a preferred embodiment, the nucleobase sequence of the compound of the invention comprises or consists, in a 5' to 3' direction i) region A: a stretch of 2-4 nucleotide analogues, followed by ii) region B: a stretch of 6-11 nucleotides (such as DNA nucleotides), which is followed by iii) region C: a stretch of 2-4 nucleotide analogues, and optionally iv) one or two nucleotides (D).

In one embodiment region A has a length of 1 nucleotide analogues. In one embodiment region A has a length of 2 nucleotide analogues. In one embodiment region A has a length of 3 nucleotide analogues. In one embodiment region A has a length of 4 nucleotide analogues. In one embodiment region C has a length of 1 nucleotide analogues. In one embodiment region C has a length of 2 nucleotide analogues. In one embodiment region C has a length of 3 nucleotide analogues. In one embodiment region C has a length of 4 nucleotide analogues. In one embodiment region B has a length of between 7 and 10 nucleotides (such as DNA nucleotides), such as 8 or 9 nucleotides (such as DNA nucleotides). In one embodiment the compound according to the invention has a length of from 12-15 nucleobases. In one embodiment the compound according to the invention has a length of 12, 13, or 14 nucleobases. In one embodiment, the gapmer may be of formula in a 5' to 3' direction D-A-B-C.

Internucleoside Linkages

In one embodiment the nucleobase sequence of the compound of the invention comprises a internucleobase linkage group selected from the group consisting of a phosphate group, a phosphodiester group, a phosphorothioate group and a boranophosphate group, the internucleoside linkage may be —O—P(O)$_2$—O—, —O—P(O, S)—O—. In one embodiment, the internucleoside linkages are in phosphate group and/or a phosphorothioate group. In a particular embodiment, all nucleotides comprise a phosphorothioate group. In one embodiment, some or all of the nucleotides are linked to each other by means of a phosphorothioate group. Suitably, all nucleotides are linked to each other by means of a phosphorothioate group.

In one embodiment, the internucleobase linkage groups between the nucleobase units of the nucleobase sequence of the compound of the invention are independently selected from either phosphorothioate or phosphodiester linkage groups.

In one embodiment region A comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions A and B.

In one embodiment region C comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions B and C. In one embodiment the internucleotide linkages between the nucleotides of region B are phosphorothioate. In one embodiment the internucleobase linkage between the 3' nucleotide analogue of A and the 5' nucleotide of region B is a phosphorothioate.

In one embodiment the internucleobase linkage between the 3' nucleotide of region B and the 5' nucleotide analogue of region C is a phosphorothioate. In one embodiment the internucleobase linkage between the 3' nucleotide analogue of A and the 5' nucleotide of region B is a phosphodiester. In one embodiment the internucleobase linkage between the 3' nucleotide of region B and the 5' nucleotide analogue of region C is a phosphodiester. In one embodiment the internucleobase linkage between the two 5' nucleotide analogues of region A are phosphodiester. In one embodiment the internucleobase linkage between the two 3' nucleotide analogues of region C are phosphodiester. In one embodiment the internucleobase linkage between the two 3' nucleotide analogues of region A are phosphodiester. In one embodiment the internucleobase linkage between the two 5' nucleotide analogues of region C are phosphodiester. In one embodiment region A has a length of 4 nucleotide analogues and internucleobase linkage between the two middle nucleotide analogues of region A are phosphodiester. In one embodiment region C has a length of 4 nucleotide analogues and internucleobase linkage between the two middle nucleotide analogues of region C are phosphodiester. In one embodiment all the internucleobase linkages between nucleotide analogues present in the compound of the invention are phosphodiester.

In one embodiment, such as the embodiments referred to above, as suitable and where not specifically indicated all remaining internucleobase linkages are either phosphodiester or phosphorothioate, or in one separate embodiment a mixture thereof. In one embodiment all the internucleobase linkage groups are phosphorothioate.

Nucleosides and Nucleoside Analogues

In some embodiments, the terms "nucleoside analogue" and "nucleotide analogue" are used interchangeably.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifiying the presence or nature of the linkages between the nucleosides.

As one of ordinary skill in the art would recognise, the 5' terminal nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

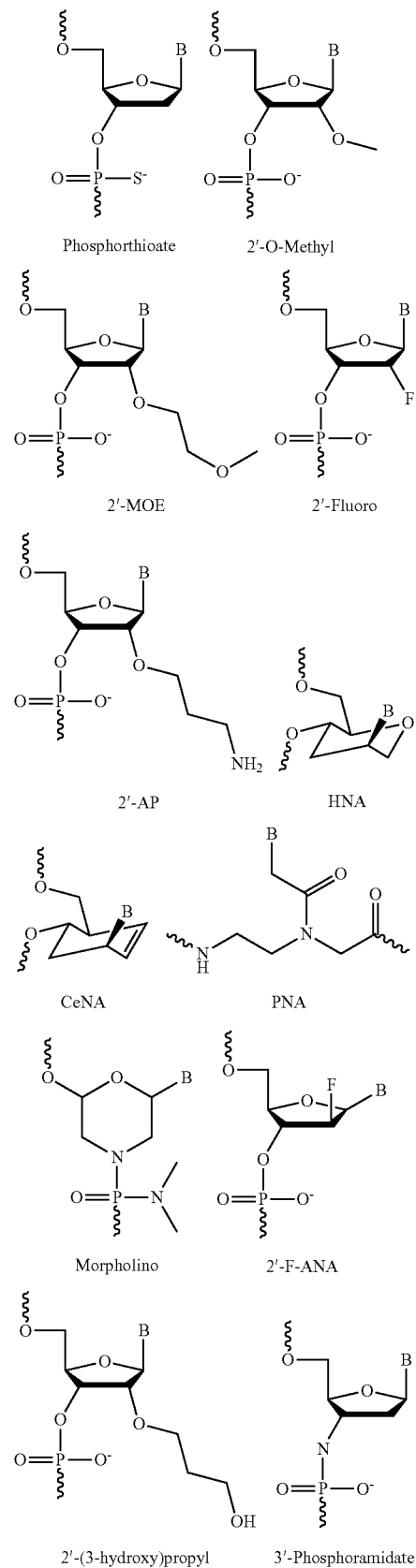

Scheme 1

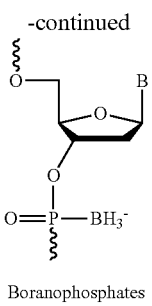

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of suitable and preferred nucleotide analogues are provided by WO2007/031091 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$, of the oligomer/target duplex (i.e. affinity enhancing nucleotide analogues).

In some embodiments, any mismatches between the nucleotide sequence of the oligomer and the target sequence are preferably found in regions outside the affinity enhancing nucleotide analogues, such as region B as referred to herein, and/or region D as referred to herein, and/or at the site of non modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention (such as in regions A and C mentioned herein) are independently selected from, for example: 2'-0-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid-Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine. In some embodiments of the invention, the oligomer may comprise both LNA and DNA units. Preferably the combined total of LNA and DNA units is 10-25, such as 10-24, preferably 10-20, such as 10-18, even more preferably 12-16. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occuring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleoside analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a linker group (such as a bridge) between C2' and C4' of the ribose sugar ring—for example as shown as the biradical $R^{4*}$—$R^{2*}$ as described below.

The LNA used in the oligonucleotide compounds of the invention preferably has the structure of the general formula I

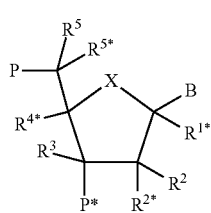

Formula 1 wherein for all chiral centers, asymmetric groups may be found in either R or S orientation; wherein X is selected from —O—, —S—, —N($R^{N*}$)—, —C($R^{6}R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent monomer, or a 5'-terminal group, such internucleotide linkage or 5'-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$), wherein for all chiral centers, asymmetric groups may be found in either R or S orientation, and;

each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; ; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^aR^b$)—C($R^aR^b$)—, C($R^aR^b$)—O—, C($R^aR^b$)—NR$^a$—, C($R^aR^b$)—S—, and C($R^aR^b$)—C($R^aR^b$)—O—, wherein each $R^a$ and $R^b$ may optionally be independently selected. In some embodiments, $R^a$ and $R^b$ may be, optionally independently selected from the group consisting of hydrogen and $_{c1-6}$alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl. For all chiral centers, asymmetric groups may be found in either R or S orientation.

In some embodiments, $R^{1*}$, $R^2$, $R^3$, $R^5$, $R^{5*}$ are hydrogen.

In some embodiments, $R^{1*}$, $R^2$, $R^3$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl. For all chiral centers, asymmetric groups may be found in either R or S orientation.

In some embodiments, $R^{1*}$, $R^2$, $R^3$ are hydrogen.

In some embodiments, $R^5$ and $R^{5*}$ are each independently selected from the group consisting of H, —CH$_3$, —CH$_2$—CH$_3$, —CH$_2$—O—CH$_3$, and —CH=CH$_2$. Suitably in some embodiments, either $R^5$ or $R^{5*}$ are hydrogen, where as the other group ($R^5$ or $R^{5*}$ respectively) is selected from the group consisting of $C_{1-5}$alkyl, $C_{2-6}$alkenyl, $C_{2-6}$alkynyl, substituted $C_{1-6}$alkyl, substituted $C_{2-6}$alkenyl, substituted $C_{2-6}$alkynyl or substituted acyl (—C(=O)—); wherein each substituted group is mono or poly substituted with substituent groups independently selected from halogen, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, OJ$_1$, SJ$_1$, NJ$_1$J$_2$, N$_3$, COOJ$_1$, CN, O—C(=O)NJ$_1$J$_2$, N(H)C(=NH)NJ$_1$J$_2$ or N(H)C(=X)N(H)J$_2$ wherein X is O or S; and each J$_1$ and J$_2$ is, independently, H, $C_{1-6}$alkyl, substituted $C_{1-6}$alkyl, $C_{2-6}$alkenyl, substituted $C_{2-6}$alkenyl, $C_{2-6}$alkynyl, substituted $C_{2-6}$alkynyl, $C_{1-6}$ aminoalkyl, substituted $C_{1-6}$ aminoalkyl or a protecting group. In some embodiments either $R^5$ or $R^{5*}$ is substituted $C_{1-6}$alkyl. In some embodiments either $R^5$ or $R^{5*}$ is substituted methylene wherein preferred substituent groups include one or more groups independently selected from F, $NJ_1J_2$, $N_3$, CN, $OJ_1$, $SJ_1$, $O-C(=O)NJ_1J_2$, $N(H)C(=NH)NJ_1J_2$ or $N(H)C(O)N(H)J_2$. In some embodiments each $J_1$ and $J_2$ is, independently H or $C_{1-6}$alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is $C(=O)NJ_1J_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from $-C(R^aR^b)-O-$, $-C(R^aR^b)-C(R^cR^d)-O-$, $-C(R^aR^b)-C(R^cR^d)-C(R^eR^f)-O-$, $-C(R^aR^b)-O-$, $-C(R^cR^d)-$, $-C(R^aR^b)-O-$, $-C(R^cR^d)-O-$, $-C(R^aR^b)-C(R^cR^d)-$, $-C(R^aR^b)-C(R^cR^d)-C(R^eR^f)-$, $-C(R^a)=C(R^b)-C(R^cR^d)-$, $-C(R^aR^b)-N(R^c)-$, $-C(R^aR^b)-C(R^cR^d)-N(R^e)-$, $-C(R^aR^b)-N(R^c)-O-$, and $-C(R^aR^b)-S-$, $-C(R^aR^b)-C(R^cR^d)-S-$, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene ($=CH_2$). For all chiral centers, asymmetric groups may be found in either R or S orientation.

In a further embodiment $R^{4*}$ and $R^{2*}$ together designate a biradical (bivalent group) selected from $-CH_2-O-$, $-CH_2-S-$, $-CH_2-NH-$, $-CH_2-N(CH_3)-$, $-CH_2-CH_2-O-$, $-CH_2-CH(CH_3)-$, $-CH_2-CH_2-S-$, $-CH_2-CH_2-NH-$, $-CH_2-CH_2-CH_2-$, $-CH_2-CH_2-CH_2-O-$, $-CH_2-CH_2-CH(CH_3)-$, $-CH=CH-CH_2-$, $-CH_2-O-CH_2-O-$, $-CH_2-NH-O-$, $-CH_2-N(CH_3)-O-$, $-CH_2-O-CH_2-$, $-CH(CH_3)-O-$, and $-CH(CH_2-O-CH_3)-O-$, and/or, $-CH_2-CH_2-$, and $-CH=CH-$. For all chiral centers, asymmetric groups may be found in either R or S orientation.

In some embodiments, $R^{4*}$ and $R^{2*}$ together designate the biradical $C(R^aR^b)-N(R^c)-O-$, wherein $R^a$ and $R^b$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl, such as hydrogen, and; wherein $R^c$ is selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl, such as hydrogen.

In some embodiments, $R^{4*}$ and $R^{2*}$ together designate the biradical $C(R^aR^b)-O-$, $-C(R^cR^d)-O-$, wherein $R^a$, $R^b$, $R^c$, and $R^d$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl, such as hydrogen.

In some embodiments, $R^{4*}$ and $R^{2*}$ form the biradical $-CH(Z)-O-$, wherein Z is selected from the group consisting of $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ^3C(=X)NJ_1J_2$ and CN, wherein each $J_1$, $J_2$ and $J_3$ is, independently, H or $C_{1-6}$alkyl, and X is O, S or $NJ_1$. In some embodiments Z is $C_{1-6}$alkyl or substituted $C_{1-6}$alkyl. In some embodiments Z is methyl. In some embodiments Z is substituted $C_{1-6}$alkyl. In some embodiments said substituent group is $C_{1-6}$alkoxy. In some embodiments Z is $CH_3OCH_2-$. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical $-CH_2-N(R^c)-$, wherein $R^c$ is $C_{1-12}$alkyloxy. In some embodiments $R^{4*}$ and $R^{2*}$ together designate a biradical -$Cq_3q_4$-NOR-, wherein $q_3$ and $q_4$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl; wherein each substituted group is, independently, mono or poly substituted with substituent groups independently selected from halogen, $OJ_1$, $SJ_1$, $NJ_1J_2$, $COOJ_1$, CN, $O-C(=O)NJ_1J_2$, $N(H)C(=NH)N J_1J_2$ or $N(H)C(=X=N(H))J_2$ wherein X is O or S; and each of $J_1$ and $J_2$ is, independently, H, $C_{1-6}$alkyl, $C_{2-6}$alkenyl, $C_{2-6}$alkynyl, $C_{1-6}$aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) $C(R^aR^b)$—O—, wherein $R^a$ and $R^b$ are each independently halogen, $C_1$-$C_{12}$alkyl, substituted $C_1$-$C_{12}$alkyl, $C_2$-$C_{12}$alkenyl, substituted $C_2$-$C_{12}$alkenyl, $C_2$-$C_{12}$alkynyl, substituted $C_2$-$C_{12}$alkynyl, $C_1$-$C_{12}$ alkoxy, substituted $C_1$-$C_{12}$alkoxy, $OJ_1$, $SJ_1$, $SOJ_1$, $SO_2J_1$, $NJ_1J_2$, $N_3$, CN, $C(=O)OJ_1$, $C(=O)NJ_1J_2$, $C(=O)J_1$, O—$C(=O)NJ_1J_2$, $N(H)C(=NH)NJ_1J_2$, $N(H)C(=O)NJ_1J_2$ or $N(H)C(=S)NJ_1J_2$; or $R^a$ and $R^b$ together are $=C(q3)(q4)$; $q_3$ and $q_4$ are each, independently, H, halogen, $C_1$-$C_{12}$alkyl or substituted $C_1$-$C_{12}$alkyl; each substituted group is, independently, mono or poly substituted with substituent groups independently selected from halogen, $C_1$-$C_6$alkyl, substituted $C_1$-$C_6$alkyl, $C_2$-$C_6$alkenyl, substituted $C_2$-$C_6$alkenyl, $C_2$-$C_6$alkynyl, substituted $C_2$-$C_6$alkynyl, $OJ_1$, $SJ_1$, $NJ_1J_2$, $N_3$, CN, $C(=O)OJ_1$, $C(=O)NJ_1J_2$, $C(=O)J_1$, O—$C(=O)N1J_1J_2$, $N(H)C(=O)NJ_1J_2$ or $N(H)C(=S)NJ_1J_2$ and; each $J_1$ and $J_2$ is, independently, H, C1-$C_6$alkyl, substituted C1-$C_6$alkyl, $C_2$-$C_6$alkenyl, substituted $C_2$-$C_6$alkenyl, $C_2$-$C_6$alkynyl, substituted $C_2$-$C_6$alkynyl, C1-$C_6$aminoalkyl, substituted C1-$C_6$aminoalkyl or a protecting group. Such compounds are disclosed in WO2009006478A, hereby incorporated in its entirety by reference.

In some embodiments, $R^{4*}$ and $R^{2*}$ form the biradical-Q-, wherein Q is $C(q_1)(q_2)C(q_3)(q_4)$, $C(q_1)=C(q_3)$, $C[=C(q_1)(q_2)]$-$C(q_3)(q_4)$ or $C(q_1)(q_2)$-$C[=C(q_3)(q_4)]$; $q_1$, $q_2$, $q_3$, $q_4$ are each independently. H, halogen, $C_{1-12}$alkyl, substituted $C_{1-12}$alkyl, $C_{2-12}$alkenyl, substituted $C_{1-12}$alkoxy, $OJ_1$, $SJ_1$, $SOJ_1$, $SO_2J_1$, $NJ_1J_2$, $N_3$, CN, $C(=O)OJ_1$, $C(=O)$—$NJ_1J_2$, $C(=O)$ $J_1$, —$C(=O)NJ_1J_2$, $N(H)C(=NH)NJ_1J_2$, $N(H)C(=O)NJ_1J_2$ or $N(H)C(=S)NJ_1J_2$; each $J_1$ and $J_2$ is, independently, H, $C_{1-6}$alkyl, $C_{2-6}$alkenyl, $C_{2-6}$alkynyl, $C_{1-6}$aminoalkyl or a protecting group; and, optionally wherein when Q is $C(q_1)(q_2)(q_3)(q_4)$ and one of $q_3$ or $q_4$ is $CH_3$ then at least one of the other of $q_3$ or $q_4$ or one of $g_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$alkyl, substituted $C_{1-6}$alkyl, $C_{2-6}$alkenyl, substituted $C_{2-6}$alkenyl, $C_{2-6}$alkynyl or substituted $C_{2-6}$alkynyl, $C_{1-6}$alkoxyl, substituted $C_{1-6}$alkoxyl, acyl, substituted acyl, $C_{1-6}$aminoalkyl or substituted $C_{1-6}$aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

In some embodiments the LNA used in the oligonucleotide compounds of the invention preferably has the structure of the general formula II:

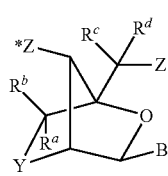

Formula II wherein Y is selected from the group consisting of —O—, —$CH_2O$—, —S—, —NH—, $N(R^e)$ and/or —$CH_2$—; Z and Z* are independently selected among an internucleotide linkage, $R^H$, a terminal group or a protecting group; B constitutes a natural or non-natural nucleotide base moiety (nucleobase), and $R^H$ is selected from hydrogen and $C_{1-4}$-alkyl; $R^a$, $R^b$ $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl) amino, carbamoyl, mono- and di($C_{1-6}$-alkyl)amino-carbonyl, amino-$C_{1-6}$-alkyl-aminocarbonyl, mono- and di($C_{1-6}$-alkyl) amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene ($=CH_2$); and $R^H$ is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$alkyl, such as methyl. For all chiral centers, asymmetric groups may be found in either R or S orientation, for example, two exemplary stereochemical isomers include the beta-D and alpha-L isoforms, which may be illustrated as follows:

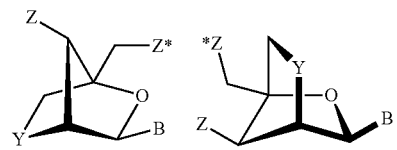

Specific exemplary LNA units are shown below:

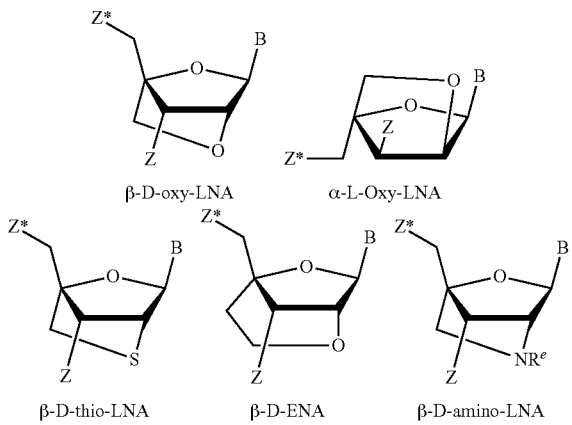

β-D-oxy-LNA     α-L-Oxy-LNA

β-D-thio-LNA     β-D-ENA     β-D-amino-LNA

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O— (where the oxygen atom of —$CH_2$—O— is attached to the 2'-position relative to the base B). $R_e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Conjugates

The invention also provides for a conjugate comprising the compound of the invention and at least one non-nucleotide or non-polynucleotide moiety covalently attached to said compound. PCT/DK2006/000512 provides suitable ligands and conjugates, which are hereby incorporated by reference.

In one embodiment of the invention, the oligonucleotide may be linked to ligands/conjugates, which may be used, e.g. to increase the cellular uptake of the oligonucleotide. This conjugation can take place at the terminal positions 5'/3'-OH but the ligands may also take place at the sugars and/or the bases. The 3'-OH is preferred site for cholesterol conjugation.

In a preferred embodiment, the oligonucleotide of the invention is conjugated with a moiety which improvise the in vivo uptake, such as cholesterol.

Thus, the oligomeric compound may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the Oligomeric compound may be arranged in dimeric or dendritic structures.

In one embodiment referring to the conjugate, the non-nucleotide or non-polynucleotide moiety consists or comprise a sterol group such as cholesterol.

Other such non-nucleotide or non-polynucleotide moieties include, but are not limited to, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

2. Pharmaceutical Compositions

The invention further provides for a pharmaceutical composition comprising a compound of the invention or a conjugate according to the invention, and a pharmaceutically acceptable diluent, carrier or adjuvant.

Pharmaceutical and other compositions comprising the oligonucleotide compounds of the invention are provided by the present invention.

The pharmaceutical composition may, in one embodiment, further comprise at least one cholesterol-lowering compound.

Suitable cholesterol lowering compounds may be selected from a compound is selected from the group consisting of bile salt sequestering resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids). Combinations with statins may be particularly preferred.

Examples of statins include Atorvastatin™, Cerivastatin™, Fluvastatin™, Lovastatin™, Mevastatin™, Pitavastatin™, Pravastatin™, Rosuvastatin™, and Simvastatin™.

The combined use of the compound of the invention and the statins may allow for a reduction in the dose of the statins, therefore overcoming side effects associated with usual dosage of statins, which include, for example, myalgias, muscle cramps, gastrointestinal symptoms, liver enzyme derangements, myositis, myopathy, rhabdomyolysis (the pathological breakdown of skeletal muscle) which may lead to acute renal failure when muscle breakdown products damage the kidney.

Fibrates, a class of amphipathic carboxylic acids is an alternative class of compound which are often combined with statin use, despite an increased frequency of rhabdomyolysis which has been reported with the combined use of statins and fribrates. The composition according to the invention may therefore further comprise firbrates, and optionally statins.

In another embodiment, compositions of the invention may contain one or more antisense compounds, particularly oligonucleotides, targeted to a first nucleic acid and one or more additional antisense compounds targeted to a second nucleic acid target.

In a method according to the invention two or more combined compounds may be used together or sequentially.

The invention also provides pharmaceutical compositions which comprise oligomeric compounds according to the invention and further compounds capable of modulating blood serum cholesterol levels, such as PCSK9 modulators, in particular antisense oligonucleotides (oligomers) targeted to PCSK9 nucleic acid targets—such as those disclosed in PCT/EP2007/060703, hereby incorporated by reference.

The invention also provides pharmaceutical compositions which comprise oligomeric compounds according to the invention and further compounds capable of modulating blood serum cholesterol levels, such as FABP4 modulators, in particular antisense oligonucleotides (oligomers) targeted to FABP4 nucleic acid targets—such as those disclosed in US provisional application 60/969,016, hereby incorporated by reference.

3. Applications

Further provided are methods of modulating the expression of apolipoprotein B in cells or tissues comprising contacting said cells or tissues with one or more of the oligonucleotide compounds or compositions of the invention. Also disclosed are methods of treating an animal or a human, suspected of having or being prone to a disease or condition, associated with expression of apolipoprotein B by administering a therapeutically or prophylactically effective amount of one or more of the oligonucleotide compounds or compositions of the invention. Further, methods of using oligonucleotide compounds for the inhibition of expression of apolipoprotein B and for treatment of diseases associated with apolipoprotein B activity are provided. Examples of such diseases are different types of HDL/LDL cholesterol imbalance; dyslipidemias, e.g., familial combined hyperlipidemia (FCHL), acquired hyperlipidemia, hypercholestorolemia; statin-resistant hypercholesterolemia; coronary artery disease (CAD) coronary heart disease (CHD) atherosclerosis.

In a preferred embodiment, acute phases of such diseases are treated, such as treatment of acute coronary syndromes, or treatment of patients newly diagnosed with one such disease, where treatment with other medicaments are not effective yet.

The invention further provides for the use of a compound or as conjugate as defined herein for the manufacture of a medicament for the treatment of abnormal levels of Apo-B100 or a disease or condition correlated thereto.

The invention further provides for a medicament comprising the compound or conjugate according to the invention for the treatment of abnormal levels of Apo-B100 or a disease or condition correlated thereto.

In one embodiment, the diseases and conditions correlated to abnormal levels of Apo-B100 may be selected from the group consisting of: atherosclerosis, hypercholesterolemia or hyperlipidemia, in example acute coronary syndromes.

The invention further provides for a method of treating a subject suffering from a disease or condition selected from atherosclerosis, hypercholesterolemia and hyperlipidemia, the method comprising the step of administering a pharmaceutical composition or conjugate as defined herein to the subject in need thereof.

The invention further provides for a method for downregulation apolipoprotein B, the method comprising the step of administering a pharmaceutical composition or conjugate as defined herein to a subject, such as the subject suffering from a medical condition selected from the group consisting of: atherosclerosis, hypercholesterolemia or hyperlipidemia or acute coronary syndrome.

Salts

The Oligomeric compound can be employed in a variety of pharmaceutically acceptable salts. As used herein, the term refers to salts that retain the desired biological activity of the LNA oligonucleotide and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or combinations, e.g., a zinc tannate salt or the like.

Such salts are formed, from the Oligomeric compound which possess phosphorodiester group and/or phosphorothioate groups, and are, for example, salts with suitable bases. These salts include, for example, nontoxic metal salts which are derived from metals of groups Ia, Ib, I a and I b of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Prodrugs

In one embodiment, the LNA oligonucleotide may be in the form of a prodrug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the prodrug approach (see e.g. Crooke, R. M. (1998) in Crooke, S. T. Antisense research and Application. Springer-Verlag, Berlin, Germany, vol. 131, pp. 103-140). In this approach, the Oligomeric compoundare prepared in a protected manner so that the Oligomeric compoundare neutral when it is administered. These protection groups are designed in such a way that they can be removed when the LNA oligonucleotide is taken up by the cells. Examples of such protection groups are S-acetylthioethyl (SATE) or S-pivaloylthioethyl (t-butyl-SATE). These protection groups are nuclease resistant and are selectively removed intracellulary.

4. Embodiments Of The Invention

The following embodiments may be combined with the features of the invention as referred to herein:

1. A medicament comprising an LNA antisense ApoB oligonucleotide for use in the treatment of acute coronary syndrome 2. A medicament comprising an LNA antisense ApoB oligonucleotide according to embodiment 1, wherein the oligonucleotide is for IV or SC administration 3. A medicament comprising an LNA antisense ApoB oligonucleotide according to any one of embodiments 1-2, wherein the oligonucleotide is for administration in a regime, wherein an initial loading dosage of up to 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 200 mg/kg, 400 mg/kg, or up to 500 mg/kg, is provided within the first two days of treatment, and wherein subsequent maintenance dosages of up to 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 20 mg/kg, 30 mg/kg, 40 mg/kg, 50 mg/kg, 100 mg/kg, 200 mg/kg, 300 mg/kg, 400 mg/kg, or up to 500 mg/kg, is provided to maintain a stable effect.

4. A medicament comprising an LNA antisense ApoB oligonucleotide according to embodiment 1, wherein the oligonucleotides are capable of hybridising against the target nucleic acid, such as an ApoB mRNA, to form a duplex with a $T_m$ of at least 30° C., such as at least 37° C., such as at least 40° C., at least 45° C., at least 50° C., at least 55° C., at least 60° C., at least 65° C., at least 70° C. In one aspect the $T_m$, is between 37° C. and 80° C., such as between 50 and 70° C., such as between 50 and 80° C. In one aspect the $T_m$ is between 30° C. and 40° C.

5. A medicament comprising an LNA antisense ApoB oligonucleotide according to any one of embodiments 1-4, wherein the dosing is adjusted to provide an effect corresponding to between 50% and 90% of steady state, such as at least 50%, 55%, 60%, 65%, 70%, 75%, 80%, 85% or at least 90% as measured by PK/PD modelling.
6. A medicament comprising an LNA antisense ApoB oligonucleotide according to any one of embodiments 1-5, wherein the dosing is adjusted to provide an effect corresponding to between 60% and 80% of steady state, such as at least 65%, 70% or 75% as measured by PK/PD modelling.
7. A medicament comprising an LNA antisense ApoB oligonucleotide according to any one of embodiments 5-6, wherein the dosing is adjusted to ensure that the desired stable level of effect is obtained within the first week of treatment, such as within 1 day, 2 days, 3, 4, 5, 6 or 7 days after onset of treatment.
8. A medicament comprising an LNA antisense ApoB oligonucleotide according to any one of embodiments 1-7, wherein the oligonucleotide is between 6 and 30 nucleotides long
9. A medicament comprising an LNA antisense ApoB oligonucleotide according to any one of embodiments 1-8, wherein the oligonucleotide is a gapmer comprising at least one LNA in each wing.
10. A medicament comprising an LNA antisense ApoB oligonucleotide according to any one of embodiments 1-9, wherein the medicament is made for use in combination with other treatment for acute coronary syndrome, such as in combination with treatment with statins.
11. A medicament according to any one of embodiments 1-10, wherein the medicament is for use in patients newly diagnosed as being in risk of having an acute coronary syndrome.
12. A method of treatment of acute coronary syndrome, wherein said method comprises the administration of an LNA antisense ApoB oligonucleotide according to any one of embodiments 1-11.
13. A method according to embodiment 12, wherein the LNA antisense ApoB oligonucleotide is administered in a dosage to achieve within the first week of treatment, at least a 60% reduction in PK/PD, such as at least 65%, 70%, 75%, 80%, 85% or at least 90%
14. A method according to any one of embodiments 1-13, wherein potential side effects on kidney and liver is monitored by masuring ALT, AST, bilirubin and creatinin, and wherein the dosage of the oligonucleotide accordingly is adjusted to avoid side effects on these organs
15. A method according to any one of embodiments 12-14, wherein the LNA antisense ApoB oligonucleotide is administered in a dosage to achieve within the first week of treatment, a reduction in PK/PD of between 60% and 80%.
16. A method according to any one of embodiments 12-15, wherein the LNA antisense ApoB oligonucleotide is used in combination with other treatment, such as in combination with statins.
17. A method according to any one of embodiments 1-16, wherein the treatment is for patients newly diagnosed as being at risk of having an acute coronary disorder.
18. A medicament according to embodiment 18, wherein the oligonucleotide comprises 2'MOE nucleotide analogues.
19. A medicament according to embodiment 18, wherein the oligonucleotide comprises both LNA nucleotide analogues and 2'MOE nucleotide analogues.
20. A medicament according to embodiments 18, wherein the ApoB antisense oligonucleotide is not an LNA antisense oligonucleotide.
21. A medicament according to any one of embodiments 1-20, wherein the oligonucleotide comprises or consists of any one of SEQ ID NO: 1-25.
22. A medicament according to any one of embodiments 1-20, wherein the medicament comprises or consists of oligonucleotide compounds over specific motifs targeting apolipoprotein B. These motifs are SEQ ID NOS: 2-15, in particular SEQ ID NOS: 5, 9 and 13 of WO2007/031081.
23. A medicament according to any one of embodiments 1-20, wherein the medicament comprises or consists of oligonucleotide compounds over specific motifs targeting apolipoprotein B. preferred motifs are SEQ ID NOS: 1-25, 52-78 and 98-112 as disclosed in Table 2 of the present application.
24. A medicament according to any one of embodiments 1-23, wherein the medicament consists or comprises SEQ ID NOS: 17-40, and/or 41-49, in particular SEQ ID NOS: 16, 17, 26 and 34 of WO2007/031081.
25. A medicament according to any one of embodiments 1-23, wherein the medicament consists or comprises SEQ ID NOS: 26-51, 79-97 and 113-137 as disclosed in Table 2 of the present application.
26. Medicament according to any one of embodiments 1-25, wherein the medicament comprises an antisense ApoB oligonucleotide which comprise a mixture of LNA and other nucleotide analogues.
27. A medicament according to embodiment 26, wherein the oligonucleotide comprise a mixture of LNA and 2'MOE.
28. A medicament according to any one of the previous embodiments, wherein the oligonucleotide is 12, 13, 14, 15 or 16 nucleotides long.

5. EXAMPLES

Example 1

LNA Monomer and Oligonucleotide Synthesis, Stability Testing, Cholesterol Measurement, mRNA Level Quantitation, Oligo Screening, In Vivo PK/PD LNA Monomer and oligonucleotide synthesis were performed using the methodology referred to in Examples 1 and 2 of WO2008/113830. The stability of LNA oligoncletides in human or rat plasma is performed using the methodology referred to in Example 4 of WO2007/112754 (incorporated by reference herein). Measurement of Cholesterol levels in plasma is done according to Example 3 of WO2008/113830. Measurement of mRNA levels is done according to Example 4 of WO2008/113830. Screening of oligonucleotides targeting apoB-100 mRNA and on cholesterol levels in animals is done according to the methodology described in Example 5-8 of WO2008/113830. The above mentioned examples of WO2008/113830 are hereby specifically incorporated by reference.

The method of cross species comparison of In Vivo PK/PD relationships has been described in Yu et al. (2008 (Nov. 14) Biochemical Pharmacology, and in Drug Metab Dispos. 2007 March; 35(3):460-8, which are both incorporated in their entirety by reference.

All references cited herein are hereby incorporated by reference in their entireties.

Example 2

Oligonucleotides Useful in the Invention

Examples of Oligonucleotides useful in the present invention are presented in Table 2 below:

TABLE 2

| Test substance | Length | Target seq |
|---|---|---|
| SEQ ID NO: 1 | 14 | 5'-TCTGAAGTCCATGA-3' |
| SEQ ID NO: 2 | 14 | 5'-GGATCAAATATAAG-3' |
| SEQ ID NO: 3 | 14 | 5'-GTTGACACTGTCTG-3' |
| SEQ ID NO: 4 | 12 | 5'-GTTGACACTGTC-3' |
| SEQ ID NO: 5 | 14 | 5'-GACTGCCTGTTCTC-3' |
| SEQ ID NO: 6 | 13 | 5'-CGTTGGAGTAAGC-3' |
| SEQ ID NO: 7 | 14 | 5'-GCGTTGGAGTAAGC-3' |
| SEQ ID NO: 8 | 14 | 5'-CTCTGTGATCCAGG-3' |
| SEQ ID NO: 9 | 14 | 5'-GGACTCTGTGATCC-3' |
| SEQ ID NO: 10 | 14 | 5'-CTGTTTGAGGGACT-3' |
| SEQ ID NO: 11 | 14 | 5'-GAGATGGCAGATGG-3' |
| SEQ ID NO: 12 | 14 | 5'-GCTGGTGTTGCCAC-3' |
| SEQ ID NO: 13 | 13 | 5'-CAGATCCTTGCAC-3' |
| SEQ ID NO: 14 | 14 | 5'-CCAGATCCTTGCAC-3' |
| SEQ ID NO: 15 | 12 | 5'-ACCTTTTGAGAC-3' |
| SEQ ID NO: 16 | 14 | 5'-CAATGTTCAGACTG-3' |
| SEQ ID NO: 17 | 14 | 5'-CCTGCAATGTTCAG-3' |
| SEQ ID NO: 18 | 14 | 5'-TAGGGCTGTAGCTG-3' |
| SEQ ID NO: 19 | 14 | 5'-GTTGGTCTACTTCA-3' |
| SEQ ID NO: 20 | 14 | 5'-CCAACCAATTTCTC-3' |
| SEQ ID NO: 21 | 14 | 5'-GTCAATTGTAAAGG-3' |
| SEQ ID NO: 22 | 14 | 5'-GTTTAAGAAATCCA-3' |
| SEQ ID NO: 23 | 12 | 5'-CTTAGTGTTAGC-3' |
| SEQ ID NO: 24 | 12 | 5'-GGTTCTTAGTGT-3' |
| SEQ ID NO: 25 | 14 | 5'-CTGGTTCTTAGTGT-3' |
| SEQ ID NO: 26 | | 5'-$G_s{}^{om}C_s{}^\circ a_s t_s g_s g_s t_s a_s t_s{}^\circ T_s{}^{om}C_s{}^\circ A^\circ$-3' |
| SEQ ID NO: 27 | | 5'-$T_s{}^{om}C_s{}^\circ T_s g_s a_s a_s g_s t_s c_s c_s a_s{}^\circ T_s{}^\circ G_s{}^\circ A^\circ$-3' |
| SEQ ID NO: 28 | | 5'-$G_s{}^\circ G_s{}^\circ A_s{}^\circ t_s c_s a_s a_s a_s t_s a_s t_s{}^\circ A_s{}^\circ A_s{}^\circ G^\circ$-3' |
| SEQ ID NO: 29 | | 5'-$G_s{}^\circ T_s{}^\circ T_s{}^\circ g_s a_s c_s a_s c_s t_s g_s t_s{}^{om}C_s{}^\circ T_s{}^\circ G^\circ$-3' |
| SEQ ID NO: 30 | | 5'-mCsoAsoAsotsgststscsasgsasmCsoTsoGo-3' |
| SEQ ID NO: 31 | | 5'-$G_s{}^\circ A_s{}^{om}C_s{}^\circ t_s g_s c_s c_s t_s g_s t_s t_s{}^{om}C_s{}^\circ T_s{}^\circ C^\circ$-3' |
| SEQ ID NO: 32 | | 5'-${}^{om}C_s{}^\circ G_s{}^\circ T_s{}^\circ t_s g_s g_s a_s g_s t_s a_s a_s G_s{}^{om}C^\circ$-3' |
| SEQ ID NO: 33 | | 5'-$G_s{}^{om}C_s{}^\circ G_s{}^\circ t_s t_s g_s g_s a_s g_s t_s a_s A_s{}^\circ G_s{}^{om}C^\circ$-3' |
| SEQ ID NO: 34 | | 5'-mCsoTsomCsotsgtsgsastscscsAsoGsoGo-3' |
| SEQ ID NO: 35 | | 5'-GsoGsoAsocstscstsgstsgsasTsomCsomCo-3' |
| SEQ ID NO: 36 | | 5'-mCsoTsoGsotststsgsasgsgsgsAsomCsoTo-3' |
| SEQ ID NO: 37 | | 5'-GsoAsoGsoastsgsgscsasgsasTsoGsoGo-3' |
| SEQ ID NO: 38 | | 5'-GsomCsoTsogsgstsgststsgscsmCsoAsomCo-3' |
| SEQ ID NO: 39 | | 5'-mCsoAsoGsoastscscststsgscsAsomCo-3' |

TABLE 2-continued

| Test substance | Length Target seq |
|---|---|
| SEQ ID NO: 40 | 5'-mCsomCsoAsogsastscscststsgsmCsoAsomCo-3' |
| SEQ ID NO: 41 | 5'-G$_s$°T$_s$°t$_s$g$_s$a$_s$c$_s$a$_s$c$_s$t$_s$g$_s$T$_s$$^{om}$C°-3' |
| SEQ ID NO: 42 | 5'-AsomCsocststststsgsasgsAsomCo-3' |
| SEQ ID NO: 43 | 5'-mCsomCsoTsogscsasastsgststsmCsoAsoGo-3' |
| SEQ ID NO: 44 | 5'-TsoAsoGsogsgscstsgstsasgsmCsoTsoGo-3' |
| SEQ ID NO: 45 | 5'-GsoTsoTsogsgstscstsascstsTsomCsoAo-3' |
| SEQ ID NO: 46 | 5'-mCsomCsoAsoascscsasastststsmCsoTsomCo-3' |
| SEQ ID NO: 47 | 5'-GsoTsomCsoasaststsgstsasasAsoGsoGo-3' |
| SEQ ID NO: 48 | 5'-GsoTsoTsotsasasgsasasastsmCsomCsoAo-3' |
| SEQ ID NO: 49 | 5'-mCsoTsotsasgstsgststsasGsomCo-3' |
| SEQ ID NO: 50 | 5'-GsoGsotstscststsasgstsGsoTo-3' |
| SEQ ID NO: 51 | 5'-mCsoTsoGsogststscststsasgsTsoGsoTo-3' |
| SEQ ID NO: 52 | 5'-GGTATTCAGTGTGATG-3' |
| SEQ ID NO: 53 | 5'-ATTGGTATTCAGTGTG-3' |
| SEQ ID NO: 54 | 5'-TTGTTCTGAATGTCCA-3' |
| SEQ ID NO: 55 | 5'-TCTTGTTCTGAATGTC-3' |
| SEQ ID NO: 56 | 5'-TGGTATTCAGTGTGAT-3' |
| SEQ ID NO: 57 | 5'-TTGGTATTCAGTGTGA-3' |
| SEQ ID NO: 58 | 5'-CATTGGTATTCAGTGT-3' |
| SEQ ID NO: 59 | 5'-GCATTGGTATTCAGTG-3' |
| SEQ ID NO: 60 | 5'-AGCATTGGTATTCAGT-3' |
| SEQ ID NO: 61 | 5'-CAGCATTGGTATTCAG-3' |
| SEQ ID NO: 62 | 5'-TCAGCATTGGTATTCA-3' |
| SEQ ID NO: 63 | 5'-TTCAGCATTGGTATTC-3' |
| SEQ ID NO: 64 | 5'-GTTCAGCATTGGTATT-3' |
| SEQ ID NO: 65 | 5'-AGTTCAGCATTGGTAT-3' |
| SEQ ID NO: 66 | 5'-AAGTTCAGCATTGGTA-3' |
| SEQ ID NO: 67 | 5'-AAAGTTCAGCATTGGT-3' |
| SEQ ID NO: 68 | 5'-ATTTCCATTAAGTTCT-3' |
| SEQ ID NO: 69 | 5'-GGTATTTCCATTAAGT-3' |
| SEQ ID NO: 70 | 5'-GACTCAATGGAAAAGT-3' |
| SEQ ID NO: 71 | 5'-ATGACTCAATGGAAAA-3' |
| SEQ ID NO: 72 | 5'-GCTAACACTAAGAACC-3' |
| SEQ ID NO: 73 | 5'-CACTAAGAACCAGAAG-3' |
| SEQ ID NO: 74 | 5'-CTAAGAACCAGAAGAT-3' |
| SEQ ID NO: 75 | 5'-TGAATCGGGTCGCATC-3' |
| SEQ ID NO: 76 | 5'-TGAATCGGGTCGCATT-3' |

TABLE 2-continued

| Test substance | Length | Target seq |
|---|---|---|
| SEQ ID NO: 77 | | 5'-GUCAUCACACUGAAUACCAAU-3' |
| SEQ ID NO: 78 | | 5'-AUUGGUAUUCAGUGUGAUGACAC-3' |
| SEQ ID NO: 79 | | 5'-G$_s$G$_s$T$_s$a$_s$t$_s$c$_s$a$_s$g$_s$t$_s$g$_s$t$_s$G$_s$A$_s$T$_s$g-3' |
| SEQ ID NO: 80 | | 5'-A$_s$T$_s$g$_s$g$_s$t$_s$a$_s$t$_s$t$_s$c$_s$a$_s$g$_s$T$_s$G$_s$T$_s$g-3' |
| SEQ ID NO: 81 | | 5'-A$_s$T$_s$G$_s$g$_s$t$_s$a$_s$t$_s$t$_s$c$_s$a$_s$g$_s$T$_s$G$_s$T$_s$g-3' |
| SEQ ID NO: 82 | | 5'-T$_s$T$_s$G$_s$T$_s$t$_s$c$_s$t$_s$g$_s$a$_s$a$_s$t$_s$g$_s$T$_s$$^{Me}$C$_s$$^{Me}$C$_s$a-3' |
| SEQ ID NO: 83 | | 5'-T$_s$$^{Me}$C$_s$T$_s$T$_s$g$_s$t$_s$t$_s$c$_s$t$_s$g$_s$a$_s$a$_s$T$_s$G$_s$T$_s$c-3' |
| SEQ ID NO: 84 | | 5'-$^{Me}$C$_s$A$_s$T$_s$T$_s$g$_s$g$_s$t$_s$a$_s$t$_s$t$_s$c$_s$a$_s$G$_s$T$_s$G$_s$t-3' |
| SEQ ID NO: 85 | | 5'-G$_s$$^{Me}$C$_s$A$_s$T$_s$t$_s$g$_s$g$_s$t$_s$a$_s$t$_s$t$_s$c$_s$A$_s$G$_s$T$_s$g-3' |
| SEQ ID NO: 86 | | 5'-A$_s$G$_s$$^{Me}$C$_s$A$_s$t$_s$t$_s$g$_s$g$_s$t$_s$a$_s$t$_s$t$_s$$^{Me}$C$_s$A$_s$G$_s$t-3' |
| SEQ ID NO: 87 | | 5'-$^{Me}$C$_s$A$_s$G$_s$c$_s$a$_s$t$_s$t$_s$g$_s$g$_s$t$_s$a$_s$t$_s$t$_s$T$_s$T$_s$$^{Me}$C$_s$A$_s$g-3' |
| SEQ ID NO: 88 | | 5'-$^{Me}$C$_s$A$_s$G$_s$$^{Me}$C$_s$a$_s$t$_s$t$_s$g$_s$g$_s$t$_s$a$_s$t$_s$t$_s$T$_s$$^{Me}$C$_s$A$_s$g-3' |
| SEQ ID NO: 89 | | 5'-A$_s$T$_s$T$_s$$_s$c$_s$c$_s$a$_s$t$_s$t$_s$a$_s$a$_s$g$_s$T$_s$T$_s$$^{Me}$C$_s$t-3' |
| SEQ ID NO: 90 | | 5'-G$_s$G$_s$T$_s$A$_s$t$_s$t$_s$c$_s$c$_s$a$_s$t$_s$t$_s$A$_s$A$_s$G$_s$t-3' |
| SEQ ID NO: 91 | | 5'-G$_s$A$_s$$^{Me}$C$_s$T$_s$c$_s$a$_s$a$_s$t$_s$g$_s$g$_s$a$_s$a$_s$A$_s$A$_s$G$_s$t-3' |
| SEQ ID NO: 92 | | 5'-A$_s$T$_s$G$_s$A$_s$c$_s$t$_s$c$_s$a$_s$a$_s$t$_s$g$_s$g$_s$A$_s$A$_s$A$_s$a-3' |
| SEQ ID NO: 93 | | 5'-G$_s$$^{Me}$C$_s$T$_s$A$_s$a$_s$c$_s$a$_s$c$_s$t$_s$a$_s$a$_s$g$_s$A$_s$A$_s$$^{Me}$C$_s$c-3' |
| SEQ ID NO: 94 | | 5'-$^{Me}$C$_s$A$_s$$^{Me}$C$_s$T$_s$a$_s$a$_s$g$_s$a$_s$a$_s$c$_s$c$_s$a$_s$G$_s$A$_s$A$_s$g-3' |
| SEQ ID NO: 95 | | 5'-$^{Me}$C$_s$T$_s$A$_s$A$_s$g$_s$a$_s$a$_s$c$_s$c$_s$a$_s$g$_s$a$_s$A$_s$G$_s$A$_s$t-3' |
| SEQ ID NO: 96 | | 5'-T$_s$G$_s$A$_s$A$_s$t$_s$c$_s$g$_s$g$_s$g$_s$t$_s$c$_s$g$_s$$^{Me}$C$_s$A$_s$T$_s$c-3' |
| SEQ ID NO: 97 | | 5'-T$_s$G$_s$A$_s$A$_s$t$_s$c$_s$g$_s$g$_s$g$_s$t$_s$c$_s$g$_s$$^{Me}$C$_s$A$_s$T$_s$t-3' |
| SEQ ID NO: 98 | | 5'-CAGC ATTG GTAT TCAG-3' |
| SEQ ID NO: 99 | | 5'-CAGC ATTG GTAT TCA-3' |
| SEQ ID NO: 100 | | 5'-AGCA TTGG TATT CAG-3' |
| SEQ ID NO: 101 | | 5'-CAGC ATTG GTAT TC-3' |
| SEQ ID NO: 102 | | 5'-AGCA TTGG TATT CA-3' |
| SEQ ID NO: 103 | | 5'-GCAT TGGT ATTC AG-3' |
| SEQ ID NO: 104 | | 5'-CAGC ATTG GTAT T-3' |
| SEQ ID NO: 105 | | 5'-AGCA TTGG TATT C-3' |
| SEQ ID NO: 106 | | 5'-GCAT TGGT ATTC A-3' |
| SEQ ID NO: 107 | | 5'-CATT GGTA TTCA G-3' |
| SEQ ID NO: 108 | | 5'-CAGC ATTG GTAT-3' |
| SEQ ID NO: 109 | | 5'-AGCA TTGG TATT-3' |
| SEQ ID NO: 110 | | 5'-GCAT TGGT ATTC-3' |
| SEQ ID NO: 111 | | 5'-CATT GGTA TTCA-3' |
| SEQ ID NO: 112 | | 5'-ATTG GTAT TCAG-3' |
| SEQ ID NO: 113 | | 5'-A$_s$G$_s$$^{Me}$C$_s$a$_s$t$_s$t$_s$g$_s$g$_s$t$_s$a$_s$t$_s$t$_s$T$_s$$^{Me}$C$_s$A$_s$g-3' |
| SEQ ID NO: 114 | | 5'-A$_s$G$_s$$^{Me}$C$_s$a$_s$t$_s$t$_s$g$_s$g$_s$t$_s$a$_s$t$_s$t$_s$T$_s$$^{Me}$C$_s$A-3' |

TABLE 2-continued

| Test substance | Length | Target seq |
|---|---|---|
| SEQ ID NO: 115 | | 5'-AG$_s$$^{Me}$C$_s$a$_s$t$_s$t$_s$g$_s$g$_s$t$_s$a$_s$t$_s$T$_s$$^{Me}$C$_s$A-3' |
| SEQ ID NO: 116 | | 5'-A$_s$G$^{Me}$C$_s$a$_s$t$_s$t$_s$g$_s$g$_s$t$_s$a$_s$t$_s$T$_s$$^{Me}$C$_s$A-3' |
| SEQ ID NO: 117 | | 5'-A$_s$G$_s$$^{Me}$Ca$_s$t$_s$t$_s$g$_s$g$_s$t$_s$a$_s$t$_s$T$_s$$^{Me}$C$_s$A-3' |
| SEQ ID NO: 118 | | 5'-A$_s$G$_s$$^{Me}$C$_s$a$_s$t$_s$t$_s$g$_s$g$_s$t$_s$a$_s$tT$_s$$^{Me}$C$_s$A-3' |
| SEQ ID NO: 119 | | 5'-A$_s$G$_s$$^{Me}$C$_s$a$_s$t$_s$t$_s$g$_s$g$_s$t$_s$a$_s$t$_s$T$^{Me}$C$_s$A-3' |
| SEQ ID NO: 120 | | 5'-A$_s$G$_s$$^{Me}$C$_s$a$_s$t$_s$t$_s$g$_s$g$_s$t$_s$a$_s$t$_s$T$^{Me}$$_s$CA-3' |
| SEQ ID NO: 121 | | 5'-AG$_s$$^{Me}$C$_s$a$_s$t$_s$t$_s$g$_s$g$_s$t$_s$a$_s$t$_s$T$_s$$^{Me}$CA-3' |
| SEQ ID NO: 122 | | 5'-AG$^{Me}$C$_s$a$_s$t$_s$t$_s$g$_s$g$_s$t$_s$a$_s$tT$^{Me}$CA-3' |
| SEQ ID NO: 123 | | 5'-G$_s$$^{Me}$C$_s$a$_s$t$_s$t$_s$g$_s$g$_s$t$_s$a$_s$t$_s$T$_s$$^{Me}$C$_s$A-3' |
| SEQ ID NO: 124 | | 5'-G$^{Me}$C$_s$a$_s$t$_s$t$_s$g$_s$g$_s$t$_s$a$_s$t$_s$T$_s$$^{Me}$C$_s$A-3' |
| SEQ ID NO: 125 | | 5'-G$_s$$^{Me}$Ca$_s$t$_s$t$_s$g$_s$g$_s$t$_s$a$_s$t$_s$T$_s$$^{Me}$C$_s$A-3' |
| SEQ ID NO: 126 | | 5'-G$_s$$^{Me}$C$_s$a$_s$t$_s$t$_s$g$_s$g$_s$t$_s$a$_s$tT$_s$$^{Me}$C$_s$A-3' |
| SEQ ID NO: 127 | | 5'-G$_s$$^{Me}$C$_s$a$_s$t$_s$t$_s$g$_s$g$_s$t$_s$a$_s$t$_s$T$^{Me}$C$_s$A-3' |
| SEQ ID NO: 128 | | 5'-G$_s$$^{Me}$C$_s$a$_s$t$_s$t$_s$g$_s$g$_s$t$_s$a$_s$t$_s$T$^{Me}$$_s$CA-3' |
| SEQ ID NO: 129 | | 5'-G$^{Me}$C$_s$a$_s$t$_s$t$_s$g$_s$g$_s$t$_s$a$_s$t$_s$T$_s$$^{Me}$CA-3' |
| SEQ ID NO: 130 | | 5'-G$^{Me}$C$_s$a$_s$t$_s$t$_s$g$_s$g$_s$t$_s$a$_s$tT$^{Me}$CA-3' |
| SEQ ID NO: 131 | | 5'-G$_s$$^{Me}$C$_s$a$_s$t$_s$t$_s$g$_s$g$_s$t$_s$a$_s$t$_s$T$_s$$^{Me}$C-3' |
| SEQ ID NO: 132 | | 5'-G$^{Me}$C$_s$a$_s$t$_s$t$_s$g$_s$g$_s$t$_s$a$_s$t$_s$T$_s$$^{Me}$C-3' |
| SEQ ID NO: 133 | | 5'-G$_s$$^{Me}$Ca$_s$t$_s$t$_s$g$_s$g$_s$t$_s$a$_s$t$_s$T$_s$$^{Me}$C-3' |
| SEQ ID NO: 134 | | 5'-G$_s$$^{Me}$C$_s$a$_s$t$_s$t$_s$g$_s$g$_s$t$_s$a$_s$tT$_s$$^{Me}$C-3' |
| SEQ ID NO: 135 | | 5'-G$_s$$^{Me}$C$_s$a$_s$t$_s$t$_s$g$_s$g$_s$t$_s$a$_s$t$_s$T$^{Me}$C-3' |
| SEQ ID NO: 136 | | 5'-G$^{Me}$C$_s$a$_s$t$_s$t$_s$g$_s$g$_s$t$_s$a$_s$t$_s$T$^{Me}$C-3' |
| SEQ ID NO: 137 | | 5'-G$^{Me}$Ca$_s$t$_s$t$_s$g$_s$g$_s$t$_s$a$_s$tT$^{Me}$C-3' |

In SEQ ID NOs: 26-51, 79-97 and 113-137, upper case letters indicates nucleotide analogue units (LNA), superscript letter "o" indicates oxy-LNA, "m" or "Me" indicates methyl C-LNA and the subscript letter "s" represents phosphorothioate linkage. Absence of "s" indicates phosphodiester linkage.

Example 3

Separation of Lipoproteins by Agarose Gel Electrophoresis

Different lipoprotein fractions were separated by agarose gel electrophoresis for lipoprotein separation (Sebia gels). Lipoproteins are separated according to charge and visualized using Sudan Black stain and quantified using Densiometric scan analysis.

Example 4

Effect and Duration of a Single Dose of SEQ ID NO 26 and SEQ ID NO 41 in C57BU6J Female Mice In this study the effect and duration of a single dose at two different concentrations of SEQ ID NO 26 or SEQ ID NO 41 were examined on total cholesterol as well as on non-HDL and HDL cholesterol in lipoprotein fractions. SEQ ID NO 26 was given at 1, 2.5 or 5 mg/kg and SEQ ID NO 41 at 1, 2.5, 5 or 10 mg/kg by intra venous or subcutaneous injections to C57BL/6J female mice. Total cholesterol was measured at different time points after injection of oligonucleotide (days 1, 3, 5, 8, 16, 24 and 32) and lipoprotein profile was determined using Sebia gels one day after injection of oligonucleotide.

Total cholesterol decreased rapidly with a dose dependent maximum effect of 40-90% obtained after 2-3 days (FIG. 1). The effect decreased slowly and total cholesterol had returned to baseline level from 16 to 32 days after injection.

Figure 2:
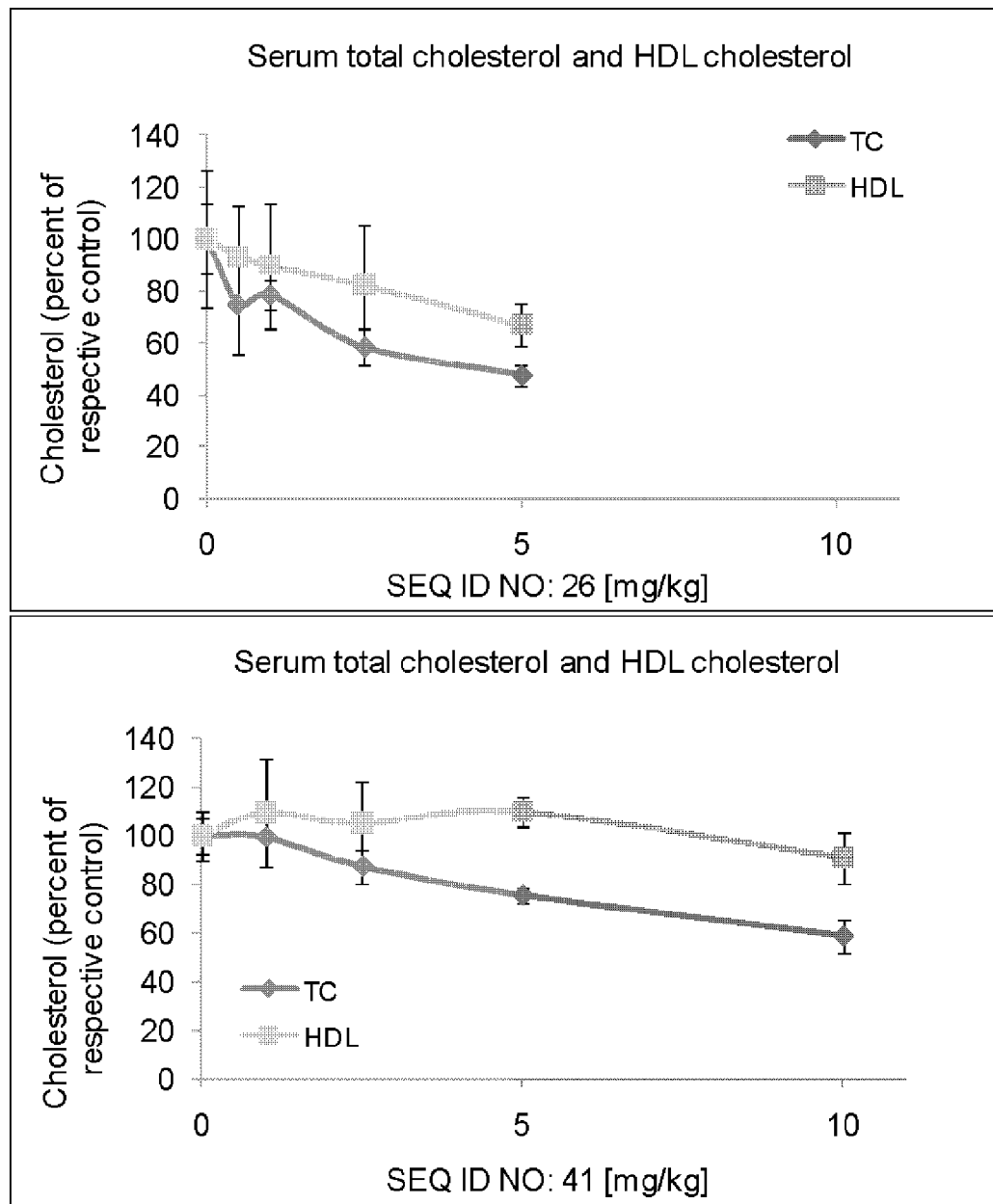

Serum total cholesterol had decreased in a dose dependent manner one day after injection. The effect on HDL was lower and for the SEQ ID NO: 41 increasing the dose from 1 to 10 mg/kg had only minor effect on HDL, indicating a specific effect on non-HDL one day after injection (FIG. 2).

The invention claimed is:

1. A method of treatment of acute coronary syndrome, comprising administering to a patient an oligonucleotide comprising GsTstsgsascsascstsgsTsmC (SEQ ID NO:41), wherein upper case letters indicate LNA, mC indicates methyl C-LNA, and the s represents phosphorothioate linkage to a patient suffering from acute coronary syndrome.

2. The method of claim 1, wherein the oligonucleotide is administered in a dosage to achieve at least a 60% reduction in PK/PD within the first week of treatment.

3. The method of claim 1, further comprising monitoring wherein potential side effects on kidney and liver is monitored by measuring ALT, AST, bilirubin and creatinine in the patient, and wherein the dosage of the oligonucleotide accordingly is adjusted to avoid side effects on these organs.

4. The method of claim 1, wherein the oligonucleotide is administered to the patient in a dosage to achieve a reduction in PK/PD of between 60% and 80% within the first week of treatment.

5. The method of claim 1, wherein the oligonucleotide is used in combination with a statin.

6. The method of claim 1 wherein the oligonucleotide is administered intravenously or subcutaneously.

7. The method of claim 1, wherein the oligonucleotide has a fast onset to reach maximum effect on total cholesterol within 7 days after onset of treatment.

8. The method of claim 1 comprising administering a loading dosage of up to 50 mg/kg followed by administering a maintenance dosages of up to 10 mg/kg.

9. The method of claim 1 further comprising administrating a statin.

10. The method of claim 1, wherein the patient is newly diagnosed as being at risk of developing acute coronary syndrome.

11. The method of claims 1-5 and 6-10 wherein the oligonucleotide is conjugated to one or more sugar residues or cholesterol.

* * * * *